United States Patent
Loccufier

(10) Patent No.: US 10,851,254 B2
(45) Date of Patent: Dec. 1, 2020

(54) PHOTOINITIATORS AND CURABLE COMPOSITIONS

(71) Applicant: AGFA NV, Mortsel (BE)

(72) Inventor: Johan Loccufier, Mortsel (BE)

(73) Assignee: AGFA NV, Mortsel (BE)

( * ) Notice: Subject to any disclaimer, the term of this patent is extended or adjusted under 35 U.S.C. 154(b) by 63 days.

(21) Appl. No.: 16/306,978

(22) PCT Filed: May 23, 2017

(86) PCT No.: PCT/EP2017/062458
§ 371 (c)(1),
(2) Date: Dec. 4, 2018

(87) PCT Pub. No.: WO2017/211587
PCT Pub. Date: Dec. 14, 2017

(65) Prior Publication Data
US 2019/0144696 A1 May 16, 2019

(30) Foreign Application Priority Data

Jun. 7, 2016 (EP) .................................. 16173227

(51) Int. Cl.
| | | |
|---|---|---|
| C09D 11/101 | (2014.01) | |
| C09D 11/38 | (2014.01) | |
| B41M 5/00 | (2006.01) | |
| C07C 329/06 | (2006.01) | |
| C07C 329/16 | (2006.01) | |
| C07F 9/32 | (2006.01) | |
| C07F 9/40 | (2006.01) | |
| C08F 4/34 | (2006.01) | |
| C08F 220/40 | (2006.01) | |
| C09D 11/30 | (2014.01) | |
| C08F 2/50 | (2006.01) | |
| B41J 11/00 | (2006.01) | |
| C08F 293/00 | (2006.01) | |

(52) U.S. Cl.
CPC ............. *C09D 11/38* (2013.01); *B41J 11/002* (2013.01); *B41M 5/0023* (2013.01); *C07C 329/06* (2013.01); *C07F 9/3258* (2013.01); *C08F 2/50* (2013.01); *C08F 4/34* (2013.01); *C08F 220/40* (2013.01); *C08F 293/005* (2013.01); *C09D 11/101* (2013.01); *C09D 11/30* (2013.01); *C08F 2438/03* (2013.01)

(58) Field of Classification Search
CPC ............................. C09D 11/38; C09D 11/101
See application file for complete search history.

(56) References Cited

U.S. PATENT DOCUMENTS

2013/0096219 A1    4/2013  Bowman et al.

FOREIGN PATENT DOCUMENTS

| CN | 103058902 A | * | 4/2013 |
|---|---|---|---|
| EP | 1 674 499 A1 | | 6/2006 |
| EP | 2 053 101 A1 | | 4/2009 |
| EP | 2 130 817 A1 | | 12/2009 |
| EP | 2 671 722 A1 | | 12/2013 |
| WO | 03/033492 A1 | | 4/2003 |
| WO | 2010/029017 A1 | | 3/2010 |
| WO | 2014/051026 A1 | | 4/2014 |
| WO | 2014/129213 A1 | | 8/2014 |
| WO | 2016/007593 A1 | | 1/2016 |

OTHER PUBLICATIONS

Islam et al., Applied Surface Science 286 (2013) 31-39.*
Official Communication issued in International Patent Application No. PCT/EP2017/062458, dated Aug. 30, 2017.
McKenzie et al., "Beyond Traditional RAFT: Alternative Activation of Thiocarbonylthio Compounds for Controlled Polymerization", Advanced Science, vol. 3, No. 9, May 17, 2016, 9 pages.
Veetil et al., "Photochemistry of S-Phenacyl Xanthates", The Journal of Organic Chemistry, vol. 76, No. 20, Oct. 21, 2011, pp. 8232-8242.
Ramakrishnan et al., "Nucleophilic Trapping of 7,11-Dideoxyanthracyclinone Quinone Methides", Journal of the American Chemical Society, vol. 105, No. 24, Nov. 1, 1983, pp. 7187-7188.

* cited by examiner

*Primary Examiner* — Vu A Nguyen
(74) *Attorney, Agent, or Firm* — Stinson LLP

(57) ABSTRACT

A specific RAFT functionalized photoinitiator and its use in radiation curable compositions, inks and inkjet inks. The specific RAFT functionalized photoinitiator can be advantageously used to reduce migrateables and bad odour.

13 Claims, No Drawings

PHOTOINITIATORS AND CURABLE COMPOSITIONS

CROSS REFERENCE TO RELATED APPLICATIONS

This application is a 371 National Stage Application of PCT/EP2017/062458, filed May 23, 2017. This application claims the benefit of European Application No. 16173227.6, filed Jun. 7, 2016, which is incorporated by reference herein in its entirety.

BACKGROUND OF THE INVENTION

1. Field of the Invention

The present invention relates to RAFT functionalized photoinitiators and their use in UV curable compositions, such as UV curable inks, especially UV curable inkjet inks.

2. Description of the Related Art

Flexographic printing systems are being increasingly replaced for packaging applications by industrial inkjet printing systems due to their flexibility in use, such as variable data printing allowing even last minute changes in the appearance of packaging when the inkjet printing system is incorporated into the production line. Radiation curable inkjet inks are particularly preferred because high quality images can be printed on non-absorbing ink-receivers, such as plastic packaging materials.

For food and pharma packaging, so-called "low migration" UV curable inkjet inks have been designed wherein the amount of migrateable compounds after UV curing is minimized. Such low migration inkjet inks are exemplified in EP 2053101 A (AGFA), EP 2671722 A (AGFA) and WO 2016/007593 A (SUN CHEMICAL). These low migration inkjet inks generally use polymerizable chemistry based on acrylates, which allows for very fast curing and minimizing migrateables.

For minimizing migration and meeting legal requirements on food safety, not only the type and amount of monomers and oligomers was carefully selected, but also specific photoinitiators were designed for the inkjet inks. A first approach was based on high molecular weight photoinitiators, such as polymeric and oligomeric photoinitiators disclosed in EP 1674499 A (AGFA), WO 03/033492 A (COATES BROTHERS) and WO 2014/129213 A (FUJI). However, their applicability in ink jet is limited by viscosity restrictions. Therefore, a second approach was developed based on polymerizable photoinitiators as disclosed in WO 2010/029017 A (AGFA), EP 2130817 A (AGFA) and WO 2014/051026 A (FUJI). Like the monomers and oligomers, the polymerizable photoinitiators were also preferably functionalized with acrylates.

However, photopolymerization of (meth)acrylates is known to generate shrinkage stress upon polymerization, which can be a cause for adhesive failure. Shrinkage stress is of particular importance in free radical UV curable ink jet inks as hardly any oligomer can be used to reduce shrinkage stress. Many strategies have been documented in the literature to cope with shrinkage stress.

Reversible addition-fragmentation chain transfer mechanisms have been used to reduce stress build up in polymer networks during photo-polymerization using different types of RAFT agents.

U.S. 2013096219 (BOWMAN) discloses methods of reducing shrinkage stress in cross-linked polymerized materials by combining a non-reactive addition-fragmentation chain transfer additive with a resin system prior to polymerization. However, for packaging applications non-reacted RAFT agents can induce problems concerning migration and set off.

There is still a need for low migration UV curable inkjet inks exhibiting reduced shrinkage stress after UV curing.

SUMMARY OF THE INVENTION

RAFT functionalized photoinitiators should be capable of combining a low viscosity with shrinkage control, if the RAFT functional group is able to interact with the propagating radicals within a timeframe of UV curing on an ink jet printer. However, complete reaction of the RAFT functionalized photoinitiator with the polymerizing network to design low migration RAFT photoinitiators is a challenge.

In order to overcome the problems described above, preferred embodiments of the present invention have been realized with very specific RAFT functionalized photoinitiators, allowing to integrate curing stress relaxing RAFT agents in radiation curable formulations without causing migration problems with the RAFT agents.

Preferred embodiments of the present invention have been realised with a photoinitiator as defined below.

It was surprisingly found that low migration properties were obtained with a photoinitiator according to Formula (I):

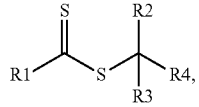

Formula (I)

wherein, R1 is selected from the group consisting of an optionally substituted alkyl group, an optionally substituted aryl or heteroaryl group, an optionally substituted alkenyl group, an optionally substituted alkynyl group, an optionally substituted alkaryl group, an optionally substituted aralkyl group, R5—O— and R6—S—; R2 is selected from the group consisting of a hydrogen, an optionally substituted alkyl group, an optionally substituted aryl or heteroaryl group, an optionally substituted alkenyl group, an optionally substituted alkynyl group, an optionally substituted alkaryl group and an optionally substituted aralkyl group; R3 is selected from the group consisting of an electron withdrawing group comprising at least one oxygen carbon double bond, a hydrogen, an optionally substituted alkyl group, an optionally substituted aryl or heteroaryl group, an optionally substituted alkenyl group, an optionally substituted alkynyl group, an optionally substituted alkaryl group and an optionally substituted aralkyl group; and R4 is selected from the group consisting of an electron withdrawing group comprising at least one oxygen carbon double bond, a nitrile group, an aryl group and a heteroaryl group; R5 and R6 are independently selected from the group consisting of an optionally substituted alkyl group, an optionally substituted aryl or heteroaryl group, an optionally substituted alkenyl group, an optionally substituted alkynyl group, an optionally substituted alkaryl group and an optionally substituted aralkyl group; with the proviso that at least one of R1 to R6 is functionalized with a photoinitiating moiety.

The specific photoinitiators can also be advantageously used in radiation curable compositions not requiring low migration properties. For example, for reducing bad odour when radiation curable compositions are used on wood based panels or textiles for interior decoration.

Hence, it is also an object of the present invention to provide radiation curable compositions comprising at least one photoinitiator according to the present invention.

It is a further object of the present invention to provide a radiation curable ink, especially a radiation curable inkjet ink, comprising at least one photoinitiator according to the present invention.

These and other objects of the present invention will become apparent from the detailed description hereinafter.

DETAILED DESCRIPTION OF THE PREFERRED EMBODIMENTS

Definitions

The term "monofunctional polymerizable compound" means that the polymerizable compound includes one polymerizable group.

The term "polyfunctional polymerizable compound" means that the polymerizable compound includes two or more polymerizable groups.

The term "alkyl" means all variants possible for each number of carbon atoms in the alkyl group i.e. methyl, ethyl, for three carbon atoms: n-propyl and isopropyl; for four carbon atoms: n-butyl, isobutyl and tertiary-butyl; for five carbon atoms: n-pentyl, 1,1-dimethyl-propyl, 2,2-dimethyl-propyl and 2-methyl-butyl, etc.

The term "substituted", in e.g. substituted alkyl group means that the alkyl group may be substituted by other atoms than the atoms normally present in such a group, i.e. carbon and hydrogen. For example, a substituted alkyl group may include a halogen atom or a thiol group. An unsubstituted alkyl group contains only carbon and hydrogen atoms.

Unless otherwise specified a substituted alkyl group, a substituted alkenyl group, a substituted alkynyl group, a substituted aralkyl group, a substituted alkaryl group, a substituted aryl and a substituted heteroaryl group are preferably substituted by one or more constituents selected from the group consisting of methyl, ethyl, n-propyl, isopropyl, n-butyl, isobutyl and tertiary-butyl, ester, amide, ether, thio-ether, ketone, aldehyde, sulfoxide, sulfone, sulfonate ester, sulphonamide, —Cl, —Br, —I, —OH, —SH, —CN and —NO$_2$.

Unless otherwise specified a substituted or unsubstituted alkyl group is preferably a C$_1$ to C$_6$-alkyl group.

Unless otherwise specified a substituted or unsubstituted alkenyl group is preferably a C$_1$ to C$_6$-alkenyl group.

Unless otherwise specified a substituted or unsubstituted alkynyl group is preferably a C$_1$ to C$_6$-alkynyl group.

Unless otherwise specified a substituted or unsubstituted aralkyl group is preferably a phenyl or naphthyl group including one, two, three or more C$_1$ to C$_6$-alkyl groups.

Unless otherwise specified a substituted or unsubstituted alkaryl group is preferably a C$_7$ to C$_{20}$-alkyl group including a phenyl group or naphthyl group.

A cyclic group includes at least one ring structure and may be a monocyclic- or polycyclic group, the latter meaning one or more rings fused together.

A heterocyclic group is a cyclic group that has atoms of at least two different elements as members of its ring(s). The counterparts of heterocyclic groups are homocyclic groups, the ring structures of which are made of carbon only. Unless otherwise specified a substituted or unsubstituted heterocyclic group is preferably a five- or six-membered ring substituted by one, two, three or four heteroatoms, preferably selected from oxygen atoms, nitrogen atoms, sulfur atoms, selenium atoms or combinations thereof.

An alicyclic group is a non-aromatic homocyclic group wherein the ring atoms consist of carbon atoms.

The term heteroaryl group means a monocyclic- or polycyclic aromatic ring comprising carbon atoms and one or more heteroatoms in the ring structure, preferably, 1 to 4 heteroatoms, independently selected from nitrogen, oxygen, selenium and sulphur. Preferred examples of heteroaryl groups include, but are not limited to, pyridinyl, pyridazinyl, pyrimidyl, pyrazyl, triazinyl, pyrrolyl, pyrazolyl, imidazolyl, (1,2,3,)- and (1,2,4)-triazolyl, pyrazinyl, pyrimidinyl, tetrazolyl, furyl, thienyl, isoxazolyl, thiazolyl, isoxazolyl, and oxazolyl. A heteroaryl group can be unsubstituted or substituted with one, two or more suitable substituents. Preferably, a heteroaryl group is a monocyclic ring, wherein the ring comprises 1 to 5 carbon atoms and 1 to 4 heteroatoms. More preferably a substituted or unsubstituted heteroaryl group is preferably a five- or six-membered ring substituted by one, two or three oxygen atoms, nitrogen atoms, sulphur atoms, selenium atoms or combinations thereof.

Unless otherwise specified an unsubstituted aryl group is preferably a phenyl group or naphthyl group.

Unless otherwise specified an acyl group is preferably a —C(=O)—R group wherein R is selected from the group consisting of an optionally substituted alkyl group, an optionally substituted aryl group, an optionally substituted heteroaryl group, an optionally substituted alkenyl group, an optionally substituted alkynyl group, an optionally substituted alkaryl group and an optionally substituted aralkyl group.

RAFT Photoinitiators

In a preferred embodiment of the invention, the photoinitiator is a compound according to Formula (I):

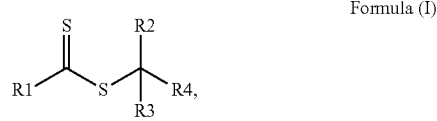

Formula (I)

wherein, R1 is selected from the group consisting of an optionally substituted alkyl group, an optionally substituted aryl or heteroaryl group, an optionally substituted alkenyl group, an optionally substituted alkynyl group, an optionally substituted alkaryl group, an optionally substituted aralkyl group, —O—R5 and —S—R6; R2 is selected from the group consisting of a hydrogen, an optionally substituted alkyl group, an optionally substituted aryl or heteroaryl group, an optionally substituted alkenyl group, an optionally substituted alkynyl group, an optionally substituted alkaryl group and an optionally substituted aralkyl group; R3 is selected from the group consisting of an electron withdrawing group comprising at least one oxygen carbon double bond, a hydrogen, an optionally substituted alkyl group, an optionally substituted aryl or heteroaryl group, an optionally substituted alkenyl group, an optionally substituted alkynyl group, an optionally substituted alkaryl group and an optionally substituted aralkyl group; and R4 is selected from the group consisting of an electron withdrawing group comprising at least one oxygen carbon double bond, a nitrile group, an aryl group and a heteroaryl group; R5 and R6 are independently selected from the group consisting of an optionally substituted alkyl group, an optionally substituted aryl or heteroaryl group, an optionally substituted alkenyl group, an optionally substituted alkynyl group, an optionally substituted alkaryl group and an optionally substituted aralkyl group; with the proviso that at least one of R1 to R6 is functionalized with a photoinitiating moiety.

In a preferred embodiment, R1 is selected from the group consisting of a substituted or unsubstituted alkyl group, a substituted or unsubstituted aryl group and a —O—R5 group, the —O—R5 group being particularly preferred, where R5 most preferably represents a substituted or unsubstituted alkyl group, a C2 to C4 alkyl group being even more preferred.

Preferred electron withdrawing groups comprising at least one carbon oxygen double bond used for R3 and R4 are selected from the group consisting of an ester group, an amide group and a ketone group. The ester group is preferably —C(=O)—O—R wherein R represents a substituted or unsubstituted alkyl group or a substituted or unsubstituted aryl group. The amide group is preferably —C(=O)—NH—R wherein R represents a substituted or unsubstituted alkyl group or a substituted or unsubstituted aryl group. The ketone group is preferably —C(=O)—R wherein R represents a substituted or unsubstituted alkyl group or a substituted or unsubstituted aryl group.

The photoinitiating moiety is preferably selected from the group consisting of a thioxanthone group, a benzophenone group, an α-hydroxyketone group, an α-aminoketone group, an acylphosphine oxide group and a phenyl glyoxalic acid ester group. If more than one photoinitiating moiety is present in the photoinitiator according to Formula (I), then these photoinitiating moieties may be the same or different. If different photoinitiating moieties are used, they are preferably independently selected from the group consisting of a thioxanthone group, a benzophenone group, an α-hydroxyketone group, an α-aminoketone group, an acylphosphine oxide group and a phenyl glyoxalic acid ester group.

In a preferred embodiment, the photoinitiator according to Formula (I):

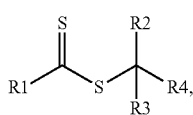

Formula (I)

is a compound wherein, R1 is selected from the group consisting of an alkyl group, an aryl group, a heteroaryl group, an alkenyl group, an alkynyl group, an alkaryl group, an aralkyl group, R5—O—, R6—S— and a photoinitiating moiety selected from the group consisting of a thioxanthone group, a benzophenone group, an α-hydroxyketone group, an α-aminoketone group, an acylphosphine oxide group and a phenyl glyoxalic acid ester group; R2 is selected from the group consisting of hydrogen, an alkyl group, an aryl group, a heteroaryl group, an alkenyl group, an alkynyl group, an alkaryl group and an aralkyl group; R3 is selected from the group consisting of —C(=O)—O—R7, —C(=O)—NR8—R9, C(=O)—R7, hydrogen, an alkyl group, an aryl group, heteroaryl group, an alkenyl group, an alkynyl group, an alkaryl group, an aralkyl group, a thioxanthone group, a benzophenone group, an α-aminoketone group, an acylphosphine oxide group and a phenyl glyoxalic acid ester group; R4 is selected from the group consisting of —C(=O)—O—R10, —C(=O)—NR11—R12, C(=O)—R10, a nitrile group, an aryl group, a heteroaryl group, a thioxanthone group, a benzophenone group, an α-aminoketone group, an acylphosphine oxide group and a phenyl glyoxalic acid ester group; and R5 and R6 are independently selected from the group consisting of an alkyl group, an aryl or heteroaryl group, an alkenyl group, an alkynyl group, an alkaryl group, an aralkyl group and a photoinitiating moiety selected from the group consisting of a thioxanthone group, a benzophenone group, an α-hydroxyketone group, an α-aminoketone group, an acylphosphine oxide group and a phenyl glyoxalic acid ester group; R7 to R10 are independently selected from the group consisting of hydrogen, an alkyl group, an aryl or heteroaryl group, an alkenyl group, an alkynyl group, an alkaryl group, an aralkyl group and a photoinitiating moiety selected from the group consisting of a thioxanthone group, a benzophenone group, an α-hydroxyketone group, an α-aminoketone group, an acylphosphine oxide group and a phenyl glyoxalic acid ester group, or R8 and R9 and/or R11 and R12 may represent the necessary atoms to form a five or six membered ring; with the proviso that at least one of R1, R3 and R4 is functionalized with a photoinitiating moiety.

The five or six membered ring formed by R8 and R9 and/or R11 is preferably selected from the group consisting of pyrrole, pyrroline, pyrrolidine, imidazole, pyridine, piperidine, morpholine, pyrazine, and piperazine.

In a particular preferred embodiment, the one or more photoinitiating moieties in the photoinitiator according to Formula (I) are independently selected from the group consisting of a thioxanthone group and an acylphosphine oxide group. Such a photoinitiator provides for excellent curing speed with UV LEDs, especially for UV LEDS having an emission wavelength higher than 360 nm.

In a preferred embodiment, the photoinitiator according to Formula (I) is functionalized with at least two RAFT functionalities. In the latter case, it should be understood that the photoinitiating moiety in Formula (I) itself includes one or more RAFT functional groups, preferably resembling the RAFT functional group shown in Formula (I). An example of such a photoinitiator is, for example, shown in Formula (II) when o represents an integer of 2 to 5.

A particularly preferred photoinitiator according to the present invention is a photoinitiator according to Formula (II):

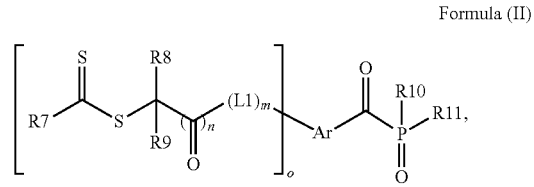

Formula (II)

wherein R7 is selected from the group consisting of an optionally substituted alkyl group, an optionally substituted aryl or heteroaryl group, an optionally substituted alkenyl group, an optionally substituted alkynyl group, an optionally substituted alkaryl group, an optionally substituted aralkyl group, —O—R5 and —S—R6; Ar represents an optionally substituted carbocyclic arylene group; L1 represents a divalent linking group comprising not more than 10 carbon atoms; R8 and R9 are independently selected from the group consisting of a hydrogen, an optionally substituted alkyl group, an optionally substituted aryl or heteroaryl group, an optionally substituted alkenyl group, an optionally substituted alkynyl group, an optionally substituted alkaryl group and an optionally substituted aralkyl group; R10 is selected from the group consisting of an optionally substituted alkyl group, an optionally substituted aryl group, an optionally substituted alkoxy group and an optionally substituted aryloxy group; R11 is selected from the group consisting of an optionally substituted alkyl group, an optionally substituted aryl group, an optionally substituted alkoxy group, an optionally substituted aryloxy group and an acyl group; n and m represents 1 or 0; o represents an integer from 1 to 5; with the proviso that if n=0 and m=1 that L1 is coupled to CR8R9 via a carbon atom of an aromatic or heteroaromatic ring.

A particular advantage of the photoinitiator according to Formula (II) is that it can also be used to reduce bad odour of a cured layer. The RAFT functional group is located on the aryl group in the photoinitiator according to Formula (II), which is known to cause bad odour upon curing due to the formation of mesitaldehyde.

Another particularly preferred photoinitiator according to the present invention is a photoinitiator according to Formula (III):

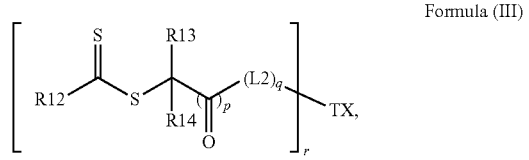

Formula (III)

wherein R12 is selected from the group consisting of an optionally substituted alkyl group, an optionally substituted aryl or heteroaryl group, an optionally substituted alkenyl group, an optionally substituted alkynyl group, an optionally substituted alkaryl group, an optionally substituted aralkyl group, —O—R5 and —S—R6; R5 and R6 are independently selected from the group consisting of an optionally substituted alkyl group, an optionally substituted aryl or heteroaryl group, an optionally substituted alkenyl group, an optionally substituted alkynyl group, an optionally substituted alkaryl group and an optionally substituted aralkyl group; L2 represents a divalent linking group comprising not more than 20 carbon atoms; TX represents an optionally substituted thioxanthone group; p and q represent 1 or 0; r represents an integer from 1 to 5; R13 and R14 are independently selected from the group consisting of a hydrogen, an optionally substituted alkyl group, an optionally substituted aryl or heteroaryl group, an optionally substituted alkenyl group, an optionally substituted alkynyl group, an optionally substituted alkaryl group and an optionally substituted aralkyl group; with the proviso that if p=0 and q=1 that L2 is coupled to CR13R14 via a carbon atom of an aromatic or heteroaromatic ring.

Another particularly preferred photoinitiator according to the present invention is a photoinitiator according to Formula (IV):

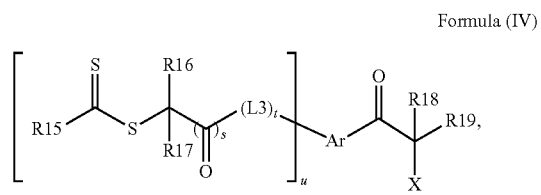

Formula (IV)

wherein R15 is selected from the group consisting of an optionally substituted alkyl group, an optionally substituted aryl or heteroaryl group, an optionally substituted alkenyl group, an optionally substituted alkynyl group, an optionally substituted alkaryl group, an optionally substituted aralkyl group, —O—R5 and —S—R6; R5 and R6 are independently selected from the group consisting of an optionally substituted alkyl group, an optionally substituted aryl or heteroaryl group, an optionally substituted alkenyl group, an optionally substituted alkynyl group, an optionally substituted alkaryl group and an optionally substituted aralkyl group; Ar represents an optionally substituted carbocyclic arylene group; L3 represents a divalent linking group comprising not more than 20 carbon atoms; R16 and R17 are independently selected from the group consisting of a hydrogen, an optionally substituted alkyl group, an optionally substituted aryl or heteroaryl group, an optionally substituted alkenyl group, an optionally substituted alkynyl group, an optionally substituted alkaryl group and an optionally substituted aralkyl group; R18 and R19 are independently selected from the group consisting of an optionally substituted alkyl group, an optionally substituted aryl group, an optionally substituted aralkyl group and an optionally substituted alkaryl group with the proviso that R18 and R19 may represent the necessary atoms to form a five to eight membered ring; X represents OH or NR20R21; R20 and R21 are independently selected from the group consisting of an optionally substituted alkyl group, an optionally substituted aryl group, an optionally substituted aralkyl group and an optionally substituted alkaryl group, with the proviso that R20 and R21 may represent the necessary atoms to form a five to eight membered ring; s and t represent 1 or 0; u represents an integer from 1 to 5; with the proviso that if s=0 and t=1 that L3 is coupled to CR16R17 via a carbon atom of an aromatic or heteroaromatic ring.

Another particularly preferred photoinitiator according to the present invention is a photoinitiator according to Formula (V):

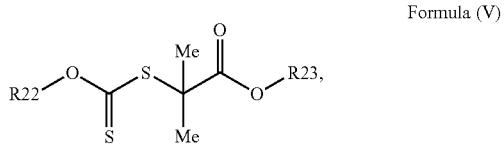

Formula (V)

wherein R22 represents an alkyl group having no more than 6 carbon atoms and R23 represents a photoinitiating moiety selected from the group consisting of an acylphosphine oxide group, a thioxanthone group, a benzophenone group, an α-hydroxy ketone group and an α-amino ketone group.
Particularly preferred examples of photoinitiators according to the present invention are given in Table 1 without being limited thereto.
TABLE 1
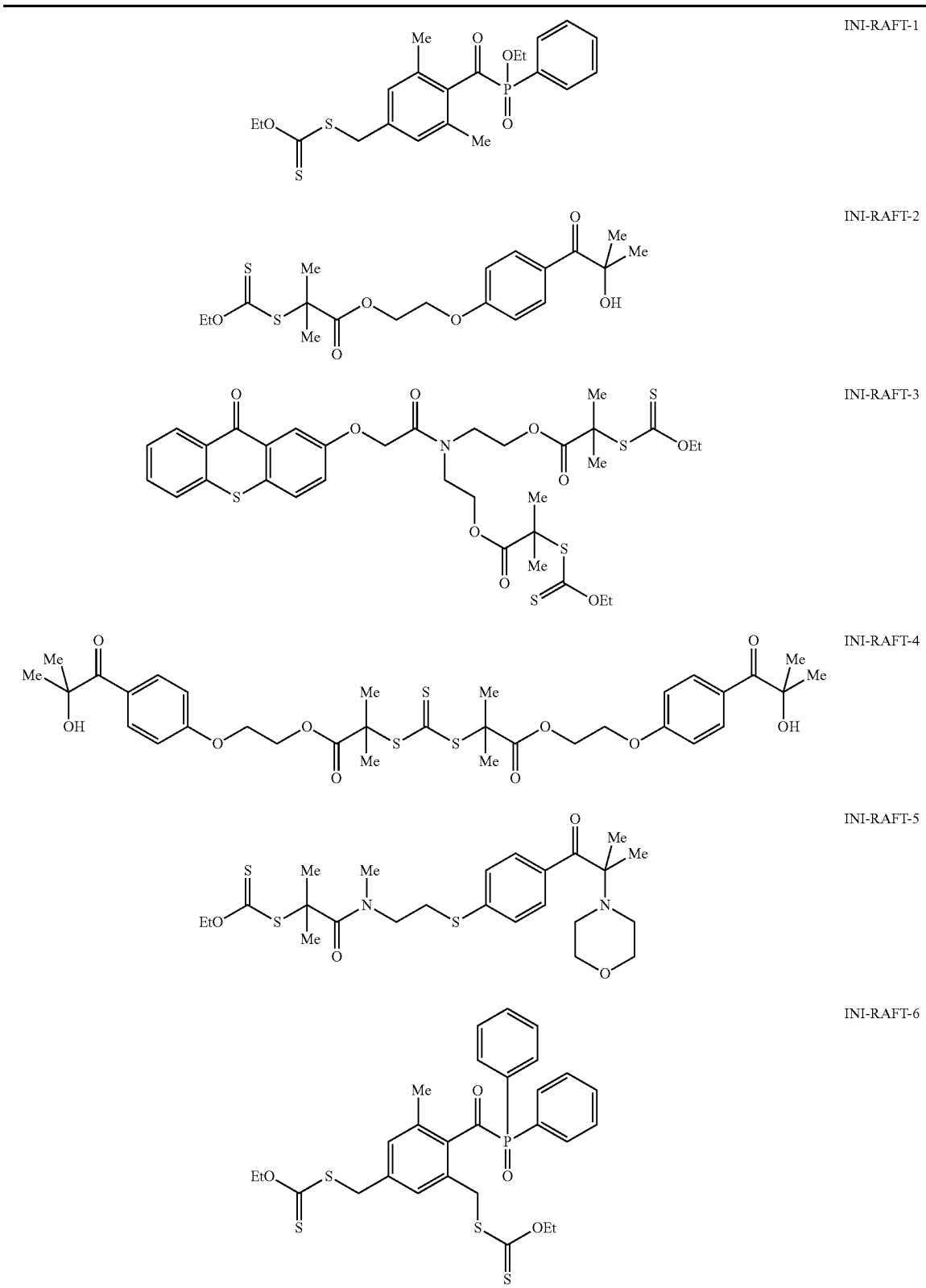

TABLE 1-continued
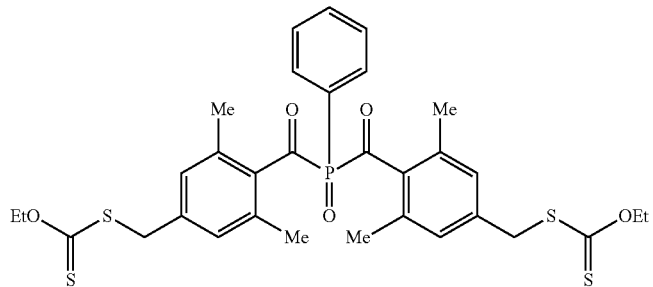 [SMILES: CCOC(=S)SCc1cc(C)c(C(=O)P(=O)(C(=O)c2c(C)cc(CSC(=S)OCC)cc2C)c2ccccc2)c(C)c1]
INI-RAFT-7
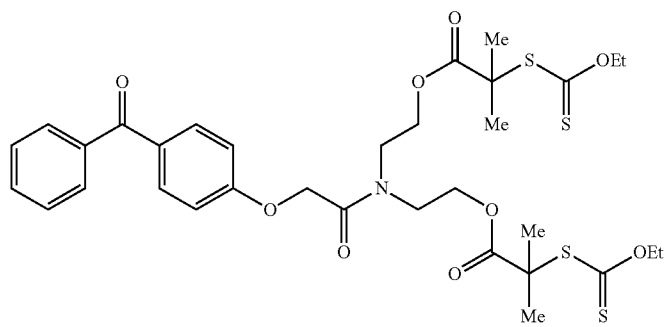 [SMILES: CCOC(=S)SC(C)(C)C(=O)OCCN(CCOC(=O)C(C)(C)SC(=S)OCC)C(=O)COc1ccc(C(=O)c2ccccc2)cc1]
INI-RAFT-8
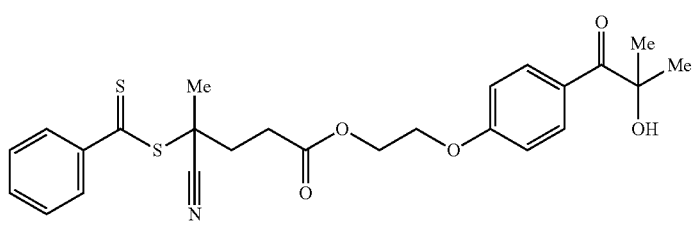 [SMILES: CC(C#N)(CCC(=O)OCCOc1ccc(C(=O)C(C)(C)O)cc1)SC(=S)c1ccccc1]
INI-RAFT-9
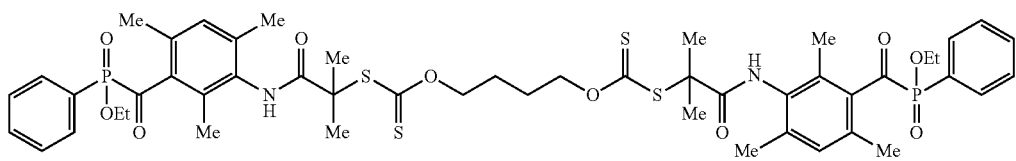 [SMILES: CCOP(=O)(C(=O)c1c(C)cc(C)c(NC(=O)C(C)(C)SC(=S)OCCCCOC(=S)SC(C)(C)C(=O)Nc2c(C)cc(C)c(C(=O)P(=O)(OCC)c3ccccc3)c2C)c1C)c1ccccc1]
INI-RAFT-10
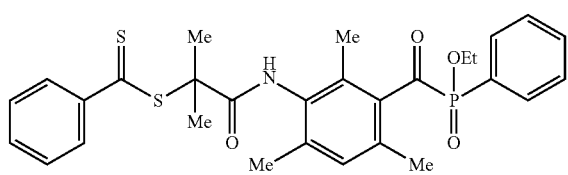 [SMILES: CCOP(=O)(C(=O)c1c(C)cc(C)c(NC(=O)C(C)(C)SC(=S)c2ccccc2)c1C)c1ccccc1]
INI-RAFT-11
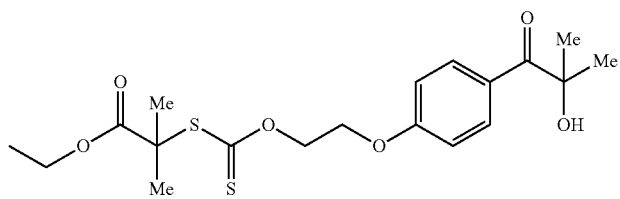 [SMILES: CCOC(=O)C(C)(C)SC(=S)OCCOc1ccc(C(=O)C(C)(C)O)cc1]
INI-RAFT-12
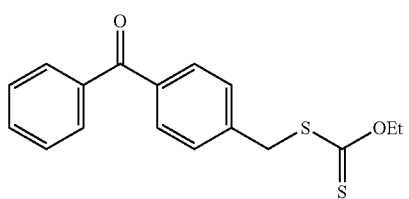 [SMILES: CCOC(=S)SCc1ccc(C(=O)c2ccccc2)cc1]
INI-RAFT-13

TABLE 1-continued
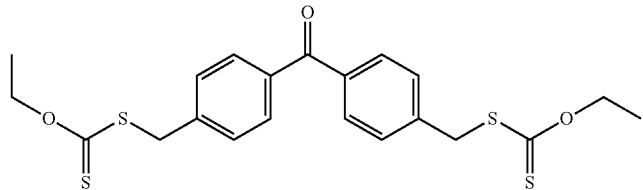 [SMILES: CCOC(=S)SCc1ccc(C(=O)c2ccc(CSC(=S)OCC)cc2)cc1]
INI-RAFT-14
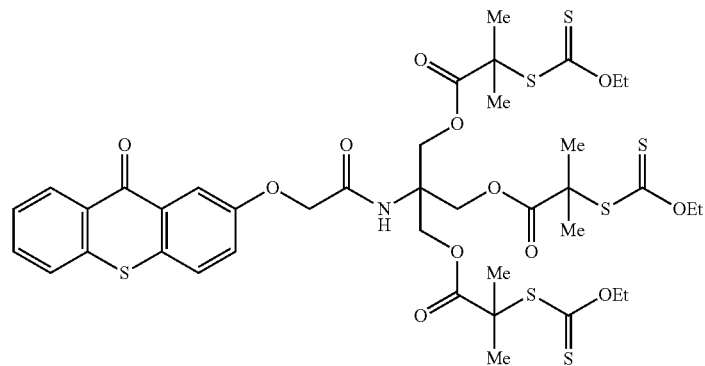 [SMILES: CCOC(=S)SC(C)(C)C(=O)OCC(COC(=O)C(C)(C)SC(=S)OCC)(COC(=O)C(C)(C)SC(=S)OCC)NC(=O)COc1ccc2sc3ccccc3c(=O)c2c1]
INI-RAFT-15
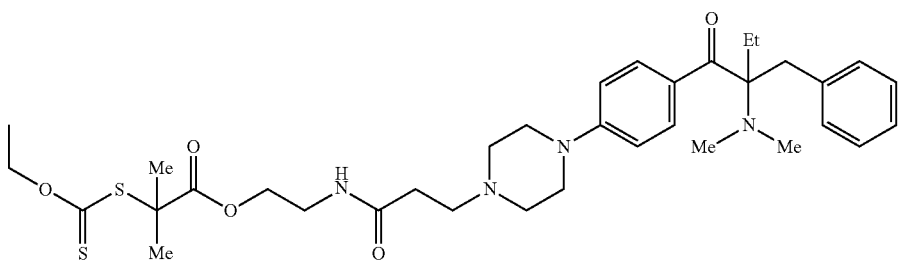 [SMILES: CCOC(=S)SC(C)(C)C(=O)OCCNC(=O)CCN1CCN(c2ccc(C(=O)C(CC)(Cc3ccccc3)N(C)C)cc2)CC1]
INI-RAFT-16
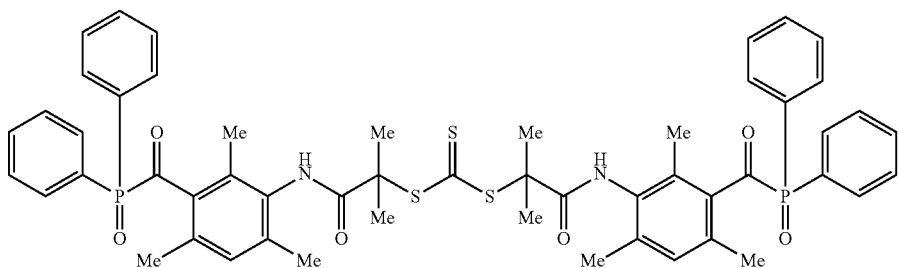 [SMILES: Cc1cc(C)c(C(=O)P(=O)(c2ccccc2)c2ccccc2)c(C)c1NC(=O)C(C)(C)SC(=S)SC(C)(C)C(=O)Nc1c(C)cc(C)c(C(=O)P(=O)(c2ccccc2)c2ccccc2)c1C]
INI-RAFT-17
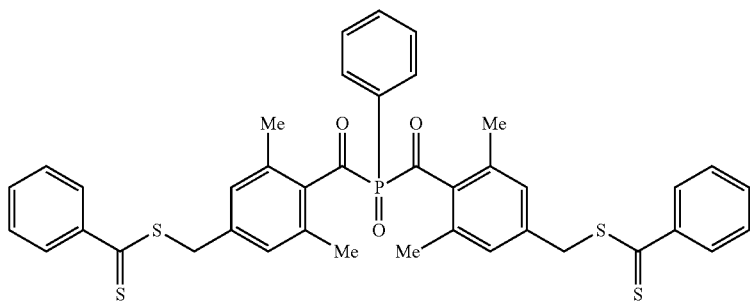 [SMILES: Cc1cc(CSC(=S)c2ccccc2)cc(C)c1C(=O)P(=O)(C(=O)c1c(C)cc(CSC(=S)c2ccccc2)cc1C)c1ccccc1]
INI-RAFT-18

TABLE 1-continued

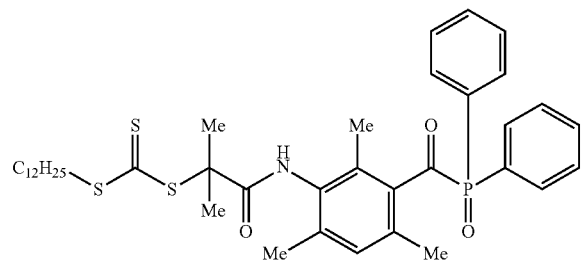

INI-RAFT-19

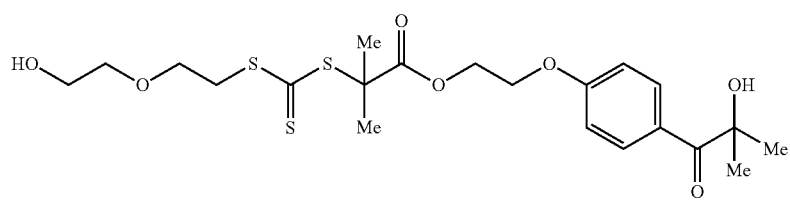 [SMILES: CC(C)(O)C(=O)c1ccc(OCCOC(=O)C(C)(C)SC(=S)SCCOCCO)cc1]

INI-RAFT-20

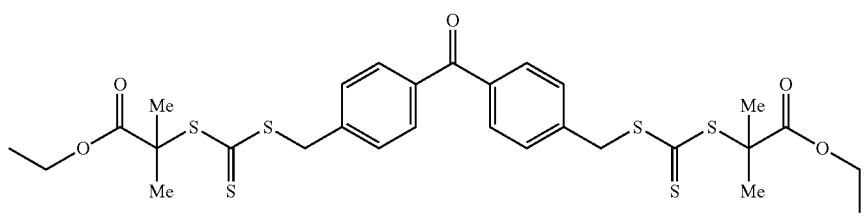 [SMILES: CCOC(=O)C(C)(C)SC(=S)SCc1ccc(C(=O)c2ccc(CSC(=S)SC(C)(C)C(=O)OCC)cc2)cc1]

INI-RAFT-21

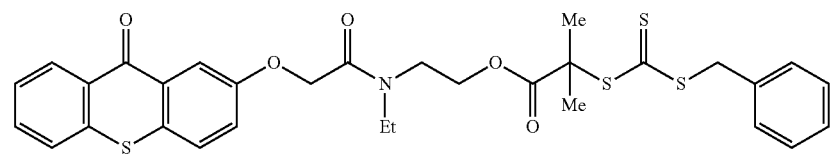 [SMILES: CCN(CCOC(=O)C(C)(C)SC(=S)SCc1ccccc1)C(=O)COc1ccc2sc3ccccc3c(=O)c2c1]

INI-RAFT-22

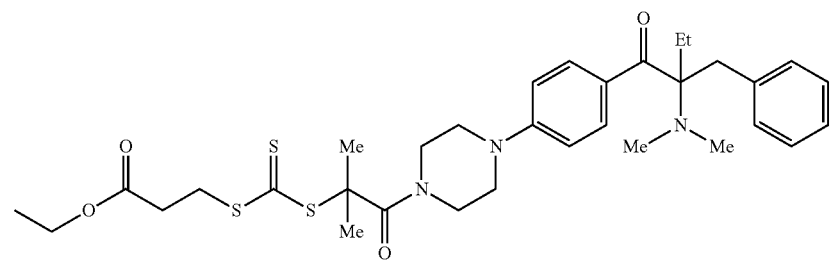 [SMILES: CCOC(=O)CCSC(=S)SC(C)(C)C(=O)N1CCN(c2ccc(C(=O)C(CC)(Cc3ccccc3)N(C)C)cc2)CC1]

INI-RAFT-23

Methods of Manufacturing the RAFT Photoinitiator

Synthetic methods for introducing a RAFT-group are well-known to the skilled person in synthetic chemistry. Methods for preparing the RAFT photoinitiator according the invention are illustrated in the examples.

A preferred method of manufacturing a photoinitiator including a reversible addition-fragmentation chain transfer group comprises the step of reacting a photoinitiator with an ethyl xanthogenate potassium salt, an ethyl xanthogenate sodium salt, an ethyl xanthogenate lithium salt, or an ethyl xanthogenate ammonium salt.

Radiation Curable Compositions and Inks

The RAFT functionalized photoinitiator of the invention can be used in any radiation curable composition, such as a UV curable coating composition and a UV curable ink, but is most advantageously used in UV curable inkjet ink.

The radiation curable compositions, inks or inkjet inks preferably include the photoinitiator according to the invention in an amount of 1 to 25 wt %, more preferably in an amount of 3 to 10 wt of the total weight of the radiation curable composition, ink or inkjet ink.

The UV curable inkjet ink may be colourless. Such an inkjet ink may be used as a primer or a varnish. A primer is usually applied for improving adhesion of an image, while a varnish is usually applied for influencing the gloss or as a protective topcoat for an image. In a more preferred embodiment, the UV curable inkjet ink contains also one or more colorants, most preferably colour pigments. A plurality of these inkjet inks may also be combined into an inkjet ink set for providing multicolour images.

The organic colour pigment is preferably dispersed in the liquid vehicle of the inkjet ink by a polymeric dispersant. The UV curable inkjet ink may contain a dispersion synergist to improve the dispersion quality and stability of the ink. Preferably, at least the magenta ink contains a dispersion synergist. A mixture of dispersion synergists may be used to further improve dispersion stability.

For printing multi-colour images, the UV curable inkjet ink is part of a UV curable inkjet ink set. A preferred UV curable inkjet ink set for printing different colours contains at least one or two but most preferably at least four UV curable inkjet inks including a photoinitiator according to the invention. The UV curable inkjet ink set is preferably a UV curable CMYK or CRYK inkjet ink set. This UV curable inkjet ink set may also be extended with extra inks such as violet, green, red, blue, and/or orange to further enlarge the colour gamut of the image. The UV curable inkjet ink set may also be extended by the combination of full density inkjet inks with light density inkjet inks. The combination of dark and light colour inks and/or black and grey inks improves the image quality by a lowered graininess.

The UV curable inkjet ink set may also include a colourless UV curable inkjet ink, such as a varnish or a primer. A varnish is used to enhance the glossiness of inkjet printed colour images. A primer can be used to improve the adhesion on difficult substrates like glass and polypropylene.

The UV curable inkjet ink set preferably also includes a UV curable white inkjet ink. The UV curable white inkjet ink preferably contains an inorganic white pigment such as a titanium dioxide, more preferably a rutile pigment, having an average particle size larger than 180 nm.

White inkjet inks are generally used for so-called "surface printing" or "backing printing" to form a reflection image on a transparent substrate. In surface printing, a white background is formed on a transparent substrate using a white ink and further thereon, a colour image is printed, where after the formed final image is viewed from the printed face. In so-called backing printing, a colour image is printed on a transparent substrate using colour inks and then a white ink is applied onto the colour inks, and the colour image is observed through the transparent substrate. In a preferred embodiment the UV curable colour inkjet ink is jetted on at least partially cured white inkjet ink. If the white ink is only partially cured, an improved wettability of the colour inkjet ink on the white ink layer is observed.

In a preferred embodiment, the UV curable inkjet ink contains an organic colour pigment in an amount of 6.0 to 13.0 wt % based on the total weight of the UV curable inkjet ink, and has a viscosity of at least 16.0 mPa·s at 45° C. and a shear rate of 10 s$^{-1}$. In a more preferred embodiment, a UV curable inkjet ink set is composed of at least three UV curable inkjet inks containing an organic colour pigment in an amount of 6.0 to 13.0 wt % based on the total weight of the UV curable inkjet ink, and each having a viscosity of at least 16.0 mPa·s at 45° C. and a shear rate of 10 s$^{-1}$.

The UV curable inkjet ink is preferably a so-called 100% solids UV curable inkjet ink. This means that no solvents, i.e. water or organic solvent, are present. However sometimes a small amount, generally less than 1 or 2 wt % of water based on the total weight of the inkjet ink, can be present. This water was not intentionally added but came into the inkjet ink via other components as a contamination, such as for example hydrophilic monomer.

The UV curable inkjet ink preferably does not contain an organic solvent. But sometimes it can be advantageous to incorporate a small amount of an organic solvent to improve adhesion to the surface of a substrate after UV-curing. In this case, the added solvent can be any amount in the range that does not cause problems of solvent resistance and VOC. The UV curable inkjet ink preferably contains 0 to 10 wt %, more preferably no more than 5.0 wt % of an organic solvent based on the total weight of the UV curable inkjet ink.

A single polymerizable compound may be used for the polymerizable composition of the UV curable inkjet ink, but usually a mixture of different polymerizable compounds to tune the ink properties, such as the adhesion to a set of substrates of the flexibility.

In one preferred embodiment of the UV curable inkjet ink, the polymerizable compound includes one or more acrylate groups. These polymerizable compounds allow for very fast curing in many industrial applications.

In another preferred embodiment of the UV curable inkjet ink, the polymerizable compound includes one or more polymerizable groups selected from the group consisting of an acrylamide, a methacrylamide, a vinyl ether group, a vinyl ester group, an allyl ether group, an allyl ester group, a vinyl carbonate group and an alkyne group. These polymerizable compounds are preferred for inkjet applications where skin irritation may represent an issue.

For food and pharma packaging, the polymerizable compound preferably includes a multifunctional hybrid monomer containing two or more different polymerizable groups per molecule, such as, for example both an acrylate group and a vinyl ether group. An especially useful monomer is 2-(2-vinyloxyethoxy)ethyl acrylate (VEEA), although other hybrid monomers such as those described in WO 2010/029017 A (AGFA) and EP 2130817 A (AGFA) would also be suitable. Preferably, the UV curable inkjet inks comprise more than 20 wt %; and more preferably more than 25 or 30 wt % of one or more hybrid multifunctional monomers, based on the total weight of polymerizable compounds.

For having a good ejecting ability, the viscosity of the UV curable inkjet ink at the jetting temperature is preferably smaller than 50.0 mPa·s, more preferably smaller than 30.0 mPa·s at a shear rate of 10 s$^{-1}$ and a jetting temperature between 30 and 70° C.

The surface tension of the UV curable inkjet ink is preferably in the range of 20 mN/m to 30 mN/m at 25° C., more preferably in the range of about 22 mN/m to about 25 mN/m at 25° C. In these ranges, good ink spreading is obtained on a wide range of substrates.

The UV curable inkjet ink may further also contain at least one inhibitor or stabilizer for improving the thermal stability of the ink.

The UV curable inkjet ink may further also contain at least one surfactant for obtaining good spreading characteristics on a substrate.

The UV curable inkjet ink is preferably a free radical curable inkjet ink. It was found that cationically curable inkjet inks posed problems of jetting reliability due to UV stray light. UV stray light hitting the nozzle plate of an inkjet print head results into failing nozzles due to clogging by cured ink in the nozzle. Unlike free radical curable ink where radical species have a much shorter lifetime, a cationic curable ink continues to cure once an acid species has been generated by UV light in the nozzle.

Other Photoinitiators and Co-initiators

In addition to the at least one RAFT photoinitiator according to the invention, the radiation curable composition or (inkjet) ink may contain one or more other photoinitiators and/or co-initiators.

For primary food packaging applications, these one or more other photoinitiators are preferably selected from the group consisting of polymerizable photoinitiators, polymeric photoinitiators and multifunctional photoinitiators. A multifunctional photoinitiator is a photoinitiator having two or more photoinitiating groups, e.g. two benzophenone groups and a thioxanthone group. In a more preferred embodiment, the one ore more other photoinitiators are a polymerizable photoinitiator. Such a photoinitiator results in a smaller viscosity than a polymeric photoinitiator while still minimizing health risks in food packaging applications.

The photoinitiator in the radiation curable composition or (inkjet) ink is a free radical initiator, more specifically a Norrish type I initiator or a Norrish type II initiator. A free radical photoinitiator is a chemical compound that initiates polymerization of monomers when exposed to actinic radiation by the formation of a free radical. A Norrish Type I initiator is an initiator which cleaves after excitation, yielding the initiating radical immediately. A Norrish type II-initiator is a photoinitiator which is activated by actinic radiation and forms free radicals by hydrogen abstraction from a second compound that becomes the actual initiating free radical. This second compound is called a polymerization synergist or a co-initiator. Both type I and type II photoinitiators can be used in the present invention, alone or in combination. The UV curable inkjet ink preferably includes no cationic photoinitiator.

The polymerizable photoinitiators may be combined with other type of non-polymeric or non-polymerizable photoinitiators, for food packaging applications at concentration levels in the inkjet ink causing no health risks, e.g. due to migration into the foodstuff.

Suitable photoinitiators are disclosed in CRIVELLO, J. V., et al. Photoinitiators for Free Radical Cationic and Anionic Photopolymerization. 2nd edition. Edited by BRADLEY, G. London, UK: John Wiley and Sons Ltd, 1998. p. 287-294.

Specific examples of photoinitiators may include, but are not limited to, the following compounds or combinations thereof: benzophenone and substituted benzophenones, 1-hydroxycyclohexyl phenyl ketone, thioxanthones such as isopropylthioxanthone, 2-hydroxy-2-methyl-1-phenylpropan-1-one, 2-benzyl-2-dimethylamino-(4-morpholinophenyl) butan-1-one, benzil dimethylketal, bis (2,6-dimethylbenzoyl)-2,4,4-trimethylpentylphosphine oxide, 2,4,6 trimethylbenzoyldiphenylphosphine oxide, 2,4,6-trimethoxybenzoyldiphenylphosphine oxide, 2-methyl-1-[4-(methylthio) phenyl]-2-morpholinopropan-1-one, 2,2-dimethoxy-1, 2-diphenylethan-1-one or 5,7-diiodo-3-butoxy-6-fluorone.

Suitable commercial photoinitiators include Irgacure™ 184, Irgacure™ 500, Irgacure™ 369, Irgacure™ 1700, Irgacure™ 651, Irgacure™ 1000, Irgacure™ 1300, Irgacure™ 1870, Irgacure™ 2959, Darocur™ 1173, Darocur™4265 and Darocur™ ITX available from BASF AG, Lucerin™ TPO available from BASF AG, Esacure™ KT046, Esacure™ KIP150, Esacure™ KT37 and Esacure™ EDB available from LAMBERTI, H-Nu™ 470 and H-Nu™ 470X available from SPECTRA GROUP Ltd.

For a low migration radiation curable composition or (inkjet) ink, the photoinitiator preferably consists of so-called diffusion hindered photoinitiator. A diffusion hindered photoinitiator is a photoinitiator which exhibits a much lower mobility in a cured layer of the radiation curable composition or (inkjet) ink than a monofunctional photoinitiator, such as benzophenone. Several methods can be used to lower the mobility of the photoinitiator. One way is to increase the molecular weight of the photoinitiators so that the diffusion speed is reduced, e.g. polymeric photoinitiators. Another way is to increase its reactivity so that it is built into the polymerizing network, e.g. multifunctional photoinitiators (having 2, 3 or more photoinitiating groups) and polymerizable photoinitiators.

The diffusion hindered photoinitiator is preferably selected from the group consisting of non-polymeric multifunctional photoinitiators, oligomeric or polymeric photoinitiators and polymerizable photoinitiators. Non-polymeric di- or multifunctional photoinitiators are considered to have a molecular weight between 300 and 900 Dalton. Non-polymerizable monofunctional photoinitiators with a molecular weight in that range are not diffusion hindered photoinitiators.

Most preferably the photoinitiators in the radiation curable composition or (inkjet) ink consist of one or more diffusion hindered photoinitiators, preferably one or more polymerizable or polymeric photoinitiators, and more preferably polymerizable photoinitiators.

Preferred diffusion hindered photoinitiators contain one or more photoinitiating functional groups derived from a Norrish type I-photoinitiator selected from the group consisting of benzoinethers, benzil ketals, α,α-dialkoxyacetophenones, α-hydroxyalkylphenones, α-aminoalkylphenones, acylphosphine oxides, acylphosphine sulphides, α-haloketones, α-halosulfones and phenylglyoxalates.

Preferred diffusion hindered photoinitiators contain one or more photoinitiating functional groups derived from a Norrish type II-initiator selected from the group consisting of benzophenones, thioxanthones, 1,2-diketones and anthraquinones.

In a particularly preferred embodiment of the radiation curable composition or (inkjet) ink, a combination of an acylphosphine oxide photoinitiator and a thioxanthone photoinitiator is used, preferably a combination wherein one or both are substituted by the RAFT group used in the invention, i.e. the acylphosphine oxide photoinitiator and/or the thioxanthone photoinitiator are represented by Formula (I).

Suitable diffusion hindered photoinitiators are also those disclosed in EP 2065362 A (AGFA) and EP 2161264 A (AGFA).

In a photoinitiating system, one of the photoinitiators can also function as a sensitizer enhancing the reactivity of another photoinitiator. Preferred sensitizers are polymerizable sensitizers such as those disclosed in EP 2053095 A (FUJIFILM).

In order to increase the photosensitivity further, the UV curable composition or inkjet ink may additionally contain co-initiators. Suitable examples of these co-initiators can be categorized in three groups: 1) tertiary aliphatic amines such as methyldiethanolamine, dimethylethanolamine, triethanolamine, triethylamine and N-methylmorpholine; (2) aromatic amines such as amylparadimethylaminobenzoate, 2-n-butoxyethyl-4-(dimethylamino) benzoate, 2-(dimethylamino)ethylbenzoate, ethyl-4-(dimethylamino) benzoate, and 2-ethylhexyl-4-(dimethylamino)benzoate; and (3) (meth)acrylated amines such as dialkylamino alkyl (meth)acrylates (e.g., diethylaminoethylacrylate) or N-morpholinoalkyl-(meth)acrylates (e.g., N-morpholinoethylacrylate). The preferred co-initiators are aminobenzoates. When one or more of these co-initiators are included into the radiation curable composition or (inkjet) ink, for food packaging applications amounts are used causing no health risks, e.g. due to migration into the foodstuff.

A combination of a polymerizable co-initiator containing a tertiary amine and a polymeric co-initiator containing a tertiary amine may be advantageously used to adjust the viscosity of the radiation curable inkjet ink.

Ethyl hexyl-4-dimethylaminobenzoate (EHA) is preferably present in the radiation curable composition or (inkjet) ink in an amount of 0.5 wt % to 5.0 wt %, more preferably in an amount of 1.0 to 4.0 wt % and most preferably 3 wt % or less, wherein all wt % are based on the total weight of the radiation curable composition or (inkjet) ink.

The at least one tertiary amine co-initiator may also be a polymerizable co-initiator containing a tertiary amine, more preferably a polymerizable co-initiator containing one or more 4-dialkylaminobenzoate groups, most preferably a polymerizable co-initiator containing one or more 4-dimethylaminobenzoate groups. Other preferred tertiary amine groups for the at least one polymerizable co-initiator containing a tertiary amine include aliphatic tertiary amine groups and piperazine groups.

The radiation curable composition or (inkjet) ink according to the present invention preferably contains the polymerizable co-initiator containing a tertiary amine in an amount of 1.0 to 10.0 wt %, more preferably 2.0 to 7.0 wt % and most preferably 3.0 to 5.0 wt % wherein all wt % are based on the total weight of the radiation curable composition or (inkjet) ink.

The at least one tertiary amine co-initiator may also be a polymeric co-initiator containing a tertiary amine, more preferably a polymeric co-initiator containing one or more 4-dialkylaminobenzoate groups, most preferably a polymeric co-initiator containing one or more 4-dimethylaminobenzoate groups. Other preferred tertiary amine groups for the at least one polymeric co-initiator containing a tertiary amine include aliphatic tertiary amine groups and piperazine groups.

In a preferred embodiment, the at least one polymeric co-initiator containing a tertiary amine is a polyether based polymer. Particularly preferred polymeric co-initiators are derivatives from ethoxylated trimethylolpropane, propoxylated trimethylolpropane, polyethylene oxide, polypropylene oxide, ethoxylated neopentyl glycol, propoxylated neopentylglycol, ethyleneoxide propylene oxide copolymers, ethoxylated glycerol, propoxylated glycerol, ethoxylated pentaerithritol, propoxylated pentaerythritol and polytetrahydrofurane.

In a further preferred embodiment, the at least one polymeric co-initiator containing a tertiary amine has a numeric average molecular weight of no more than 1500, more preferably of no more than 1000 and most preferably of no more than 750.

In a particularly preferred embodiment, the polymeric co-initiator containing a tertiary amine is selected from the group consisting of:

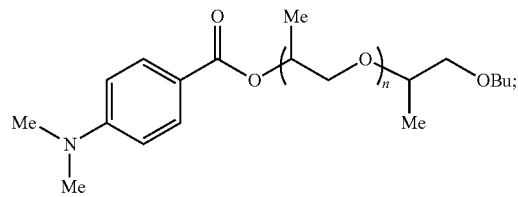

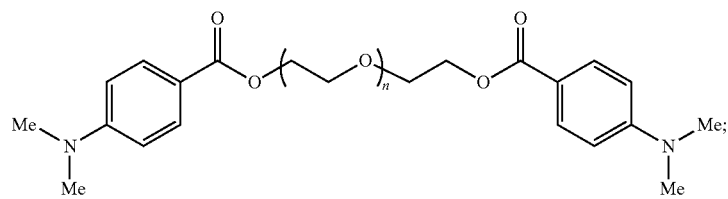

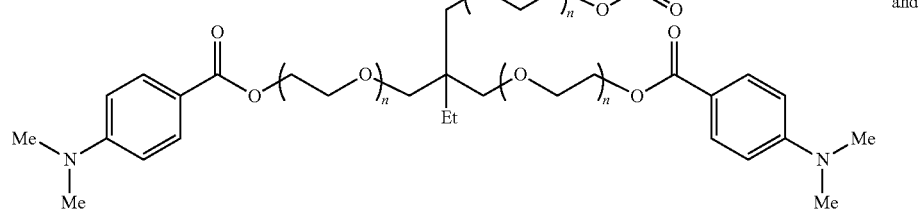

and

-continued

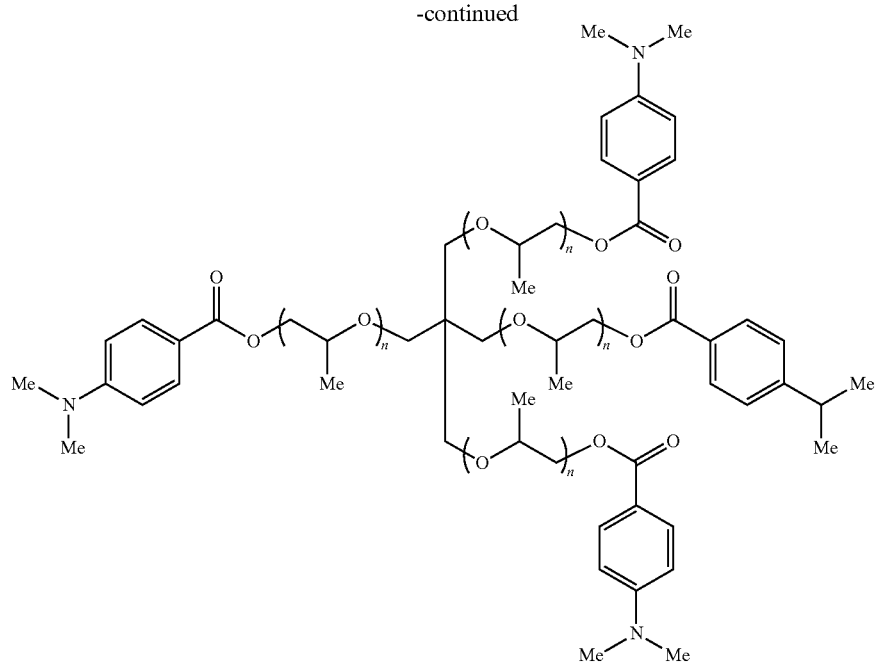

wherein the compound has a has a numeric average molecular weight of no more than 1500 or wherein n is an integer of 1 to 4.

Suitable corresponding polymeric co-initiators containing a tertiary amine are commercially available as Omnipol™ ASA (CASRN71512-90-8) from IGM Resins, Genopol™ AB-1 and AB-2 (CASRN1215019-68-3) from RAHN, and Speedcure™ 7040 (CASRN1182751-31-0) from LAMBSON.

Preferred polymeric co-initiators containing a tertiary amine are polymeric co-initiators having a dendritic polymeric architecture, more preferably a hyperbranched polymeric architecture. Preferred hyperbranched polymeric co-initiators are those disclosed in U.S. 2006014848 (AGFA).

The radiation curable composition or (inkjet) ink preferably includes the other co-initiator in an amount of 0.1 to 30.0 wt %, more preferably in an amount of 0.5 to 10.0 wt %, most preferably in an amount of 1.0 to 5.0 wt % of the total weight of the radiation curable composition or inkjet ink.

The radiation curable composition or (inkjet) ink preferably does not include a photoinitiator selected from the group of 2-hydroxy 2-methyl propiophenone, benzophenone, 2-methyl benzophenone, 4-methyl benzophenone, 2,4,6-trimethylbenzo-phenone, 1-hydroxycyclohexyl phenylketone, 2,2-dimethoxy 2-phenyl acetophenone, 2-methyl 4'-(methylthio) 2-morpholinopropiophenone, 4-isopropyl 9H-thioxanthen-9-one, 2-isopropyl 9H-thioxanthen-9-one, and 2,4-diethyl 9H-thioxanthen-9-one. Such a radiation curable composition or (inkjet) ink has no doubtful toxicology.

Polymerizable Compounds

Any polymerizable compound commonly known in the art may be employed. The polymerizable compound may be any monomer and/or oligomer found in the Polymer Handbook Vol 1+2, 4th edition, edited by J. BRANDRUP et al., Wiley-Interscience, 1999. An oligomer in the present invention is understood to contain 2 to 8 repeating monomeric units.

Preferably a monomer or oligomer capable of free radical polymerization is used as polymerizable compound. A combination of monomers, oligomers and/or prepolymers may also be used. The monomers, oligomers and/or prepolymers may possess different degrees of functionality, and a mixture including combinations of mono-, di-, tri- and higher functionality monomers, oligomers and/or prepolymers may be used. The viscosity of the radiation curable compositions and (inkjet) inks can be adjusted by varying the ratio between the monomers and oligomers.

Preferred monomers and oligomers are those listed in [0106] to [0115] in EP 1911814 A (AGFA).

A monofunctional polymerizable compound is generally used for enhancing the flexibility of a cured layer, whereas a polyfunctional polymerizable compound is used for enhancing scratch resistance of the cured layer.

A monofunctional polymerizable compound contains a single polymerizable group, preferably a free radical polymerizable group selected from the group consisting of an acrylate, a methacrylate, an acrylamide, a methacrylamide, a styrene group, a maleate, a fumarate, an itaconate, a vinyl ether, a vinyl ester, an allyl ether and an allyl ester.

In a preferred embodiment, the monofunctional polymerizable compounds are selected from acrylic acid, methacrylic acid, maleic acid (or there salts), maleic anhydride, alkyl(meth)acrylates (linear, branched and cycloalkyl) such as methyl(meth)acrylate, n-butyl(meth)acrylate, tert-butyl (meth)acrylate, cyclohexyl(meth)acrylate, and 2-ethylhexyl (meth)acrylate; aryl(meth)acrylates such as benzyl(meth) acrylate, and phenyl(meth)acrylate; hydroxyalkyl(meth) acrylates such as hydroxyethyl(meth)acrylate, and hydroxypropyl(meth)acrylate; (meth)acrylates with other types of functionalities (e.g. oxiranes, amino, fluoro, polyethylene oxide, phosphate substituted) such as glycidyl (meth)acrylate, dimethylaminoethyl(meth)acrylate, trifluoroethyl acrylate, methoxypolyethyleneglycol (meth)acrylate, and tripropyleneglycol (meth)acrylate phosphate; allyl derivatives such as allyl glycidyl ether; styrenics such as styrene, 4-methylstyrene, 4-hydroxystyrene, 4-acetostyrene, and styrenesulfonic acid; (meth)acrylonitrile; (meth)acrylamides (including N-mono and N,N-disubstituted) such as N-benzyl (meth)acrylamide; maleimides such as N-phenyl maleimide; vinyl derivatives such as vinylcaprolactam, vinylpyrrolidone, vinylimidazole, vinylnapthalene, and vinyl halides; vinylethers such as vinylmethyl ether; vinylesters of carboxylic acids such as vinylacetate, vinylbutyrate, and vinyl benzoate. In a more preferred embodiment, the monofunctional polymerizable compounds are selected from monoacrylates and vinyllactams, such as N-vinylcaprolactam. Particularly preferred monofunctional polymerizable compounds are selected from the group consisting of isoamyl acrylate, stearyl acrylate, lauryl acrylate, octyl acrylate, decyl acrylate, isoamyl acrylate, isostearyl acrylate, 2-ethylhexyl-diglycol acrylate, 2-hydroxybutyl acrylate, 2-acryloyloxyethylhexahydrophthalic acid, butoxyethyl acrylate, ethoxydiethylene glycol acrylate, methoxydiethylene glycol acrylate, methoxypolyethylene glycol acrylate, methoxypropylene glycol acrylate, phenoxyethyl acrylate, tetrahydrofurfuryl acrylate, isobornyl acrylate, 2-hydroxyethyl acrylate, 2-hydroxypropyl acrylate, 2-hydroxy-3-phenoxypropyl acrylate, vinyl ether acrylate, 2-acryloyloxyethylsuccinic acid, 2-acryloyxyethylphthalic acid, 2-acryloxyethyl-2-hydroxyethyl-phthalic acid, lactone modified flexible acrylate, t-butylcyclohexyl acrylate, caprolactone acrylate, cyclic trimethylolpropane formal acrylate, cyclic trimethylolpropane formal acrylate, ethoxylated nonyl phenol acrylate, isodecyl acrylate, isooctyl acrylate, octyldecyl acrylate, alkoxylated phenol acrylate, tridecyl acrylate and acryloylmorpholine.

In a preferred embodiment, the monofunctional polymerizable compound is selected from monoacrylates and vinyllactams, such as N-vinylcaprolactam.

The N-vinyllactam is preferably a compound represented by Formula (A):

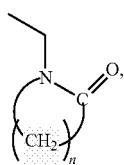

Formula (A)

wherein n denotes an integer of 2 to 6; n is preferably an integer of 3 to 5 from the viewpoint of flexibility after the ink composition is cured, adhesion to a substrate, and ready availability of starting materials, n is more preferably 3 or 5, and n is particularly preferably 5, which is N-vinylcaprolactam. N-vinylcaprolactam is preferable since it is readily available at a relatively low price, and gives particularly good ink curability and adhesion of a cured film to a recording medium.

The N-vinyllactam may have a substituent such as an alkyl group or an aryl group on the lactam ring, and may have a saturated or unsaturated ring structure bonded to the lactam ring. The compound represented by Formula (a) may be used singly or in a combination of two or more compounds.

For certain applications a limited amount or no monofunctional (meth)acrylates are employed. For example, when the substrate is a textile that is worn directly on the human skin it may give rise to skin sensitization. In such a case, the monomers and oligomers are preferably selected from a group comprising or consisting of vinyls, acrylamides, methacrylamides, vinyl carbonates, vinyl ethers, vinyl esters, vinyl carbamates, allyl ethers, allyl esters and their corresponding alkyne compounds. Particularly preferred are polymerizable compounds including an allyl ether group, vinyl carbonate group and alkyne group.

A polyfunctional polymerizable compound contains two, three or more polymerizable groups, preferably free radical polymerizable groups selected from the group consisting of an acrylate, a methacrylate, an acrylamide, a methacrylamide, a styrene group, a maleate, a fumarate, an itaconate, a vinyl ether, a vinyl ester, an allyl ether and an allyl ester.

In a preferred embodiment, the polyfunctional polymerizable compound is a duofunctional acrylate containing two polymerizable groups, namely two acrylate groups.

Preferred polyfunctional acrylates include triethylene glycol diacrylate, tetraethylene glycol diacrylate, polyethylene glycol diacrylate, dipropylene glycol diacrylate, tripropylene glycol diacrylate, polypropylene glycol diacrylate, 1,4-butanediol diacrylate, 1,6-hexanediol diacrylate, 1,9-nonanediol diacrylate, neopentyl glycol diacrylate, dimethyloltricyclodecane diacrylate, bisphenol A EO (ethylene oxide) adduct diacrylate, bisphenol A PO (propylene oxide) adduct diacrylate, hydroxypivalate neopentyl glycol diacrylate, propoxylated neopentyl glycol diacrylate, alkoxylated dimethyloltricyclodecane diacrylate and polytetramethylene glycol diacrylate, trimethylolpropane triacrylate, EO modified trimethylolpropane triacrylate, tri (propylene glycol) triacrylate, caprolactone modified trimethylolpropane triacrylate, pentaerythritol triacrylate, pentaerythritol tetraacrylate, pentaerythritolethoxy tetraacrylate, dipentaerythritol hexaacrylate, ditrimethylolpropane tetraacrylate, glycerolpropoxy triacrylate, and caprolactam modified dipentaerythritol hexaacrylate.

Other suitable difunctional acrylates include alkoxylated cyclohexanone dimethanol diacrylate, alkoxylated hexanediol diacrylate, dioxane glycol diacrylate, dioxane glycol diacrylate, cyclohexanone dimethanol diacrylate, diethylene glycol diacrylate and neopentyl glycol diacrylate.

Other polyfunctional acrylates include propoxylated glycerine triacrylate and propoxylated trimethylolpropane triacrylate, di-trimethylolpropane tetraacrylate, dipentaerythritol pentaacrylate, ethoxylated pentaerythritol tetraacrylate, methoxylated glycol acrylates and acrylate esters.

Preferred polyfunctional acrylates include dipropylene glycol diacrylate, tripropylene glycol diacrylate, 1,6-hexanediol diacrylate, cyclohexanone dimethanol diacrylate, polyethyleneglycol 200 diacrylate, 3-methyl 1,5-pentanediol diacrylate, pentaerythritol tetraacrylate, trimethylolpropane triacrylate and dipentaerythritol pentaacrylate.

The polyfunctional polymerizable compound may have two different polymerizable groups, such as a vinylether group and an acrylate group. Preferred vinylether acrylates are those disclosed in U.S. Pat. No. 6,310,115 (AGFA). A particularly preferred compound is 2-(2'-vinyloxyethoxy) ethyl acrylate (VEEA). Other suitable vinylether acrylates are those disclosed in columns 3 and 4 of U.S. 67/679,890 B (NIPPON SHOKUBAI).

Instead of difunctional or polyfunctional acrylates, also their methacrylate analogues may be used.

For food and pharma packaging applications, the radiation curable composition or (inkjet) ink preferably contains at least one monomer comprising at least one vinyl ether group and at least one polymerizable group selected from the group consisting of an acrylate group and a methacrylate group, wherein this monomer is preferably represented by Formula (B):

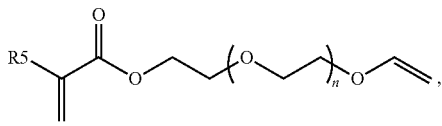

Formula (B)

wherein:

$R^5$ represents a hydrogen or a methyl group; and n represents an integer from 0 to 4. Most preferably R5 represents hydrogen.

In a preferred embodiment, the at least one monomer comprising at least one vinyl ether group and at least one (meth)acrylate group is preferably selected from the group consisting of:

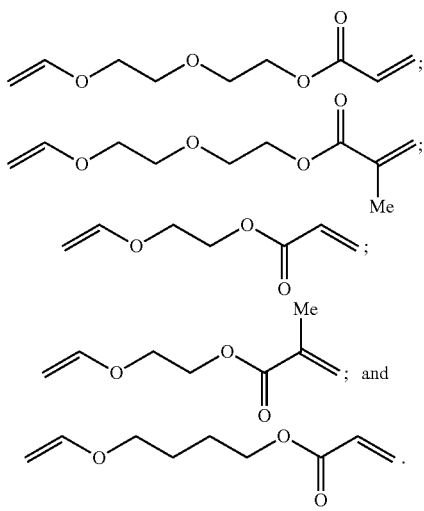

In the most preferred embodiment of the radiation curable composition or (inkjet) ink, the at least one monomer comprising at least one vinyl ether group and at least one polymerizable group selected from the group consisting of an acrylate group and a methacrylate group is 2-(2'-vinyloxyethoxy)ethyl acrylate.

Other suitable vinylether (meth)acrylates are those disclosed in columns 3 and 4 of U.S. Pat. No. 6,767,980 (NIPPON SHOKUBAI).

A single compound or a mixture of vinylether acrylates may be used.

The radiation curable composition or (inkjet) ink according to the present invention contains at least 10 wt %, more preferably at least 20 wt % and most preferably at least 25 wt % of the monomer according to Formula (A), wherein all wt % are based on the total weight of the radiation curable composition or (inkjet) ink.

In a particularly preferred embodiment, the radiation curable inkjet ink includes a polymerizable composition consisting essentially of: a) 25 to 100 wt % of a monomer according to Formula (B), preferably 2-(2-vinyloxyethoxy) ethyl acrylate; b) 0 to 55 wt % of one or more polymerizable compounds A selected from the group consisting of monofunctional acrylates and difunctional acrylates; and c) 0 to 55 wt % of one or more polymerizable compounds B selected from the group consisting of trifunctional acrylates, tetrafunctional acrylates, pentafunctional acrylates and hexafunctional acrylates, with the proviso that if the weight percentage of compounds A>24 wt %, then the weight percentage of compounds B>1 wt %; and wherein all weight percentages of A and B are based upon the total weight of the polymerizable composition.

Colorants

The radiation curable (inkjet) ink may contain a colorant. Colorants used in the curable inks may be dyes, pigments or a combination thereof. Organic and/or inorganic pigments may be used.

The colorant is preferably a pigment or a polymeric dye, most preferably a colour pigment. In food packaging applications, low molecular weight dyes, e.g. smaller than 1000 Dalton, can still migrate into the food or be extracted by the food giving undesired coloration of the food, or even worse allergic reactions after consuming the solid or liquid food.

The pigments may be black, white, cyan, magenta, yellow, red, orange, violet, blue, green, brown, mixtures thereof, and the like. This colour pigment may be chosen from those disclosed by HERBST, Willy, et al. Industrial Organic Pigments, Production, Properties, Applications. 3rd edition. Wiley—VCH, 2004. ISBN 3527305769.

Particular preferred pigments are C.I. Pigment Yellow 1, 3, 10, 12, 13, 14, 17, 55, 65, 73, 74, 75, 83, 93, 97, 109, 111, 120, 128, 138, 139, 150, 151, 154, 155, 175, 180, 181, 185, 194 and 213.

Particular preferred pigments are C.I. Pigment Red 17, 22, 23, 41, 48:1, 48:2, 49:1, 49:2, 52:1, 57:1, 88, 112, 122, 144, 146, 149, 170, 175, 176, 184, 185, 188, 202, 206, 207, 210, 216, 221, 248, 251, 254, 255, 264, 266, 270 and 272.

Particular preferred pigments are C.I. Pigment Violet 19, 23, 32, and 37.

Particular preferred pigments are C.I. Pigment Blue 15:1, 15:2, 15:3, 15:4, 15:6, 16, 56, 61 and (bridged) aluminium phthalocyanine pigments.

Particular preferred pigments are C.I. Pigment Orange 5, 13, 16, 34, 40, 43, 59, 66, 67, 69, 71 and 73.

Particular preferred pigments are C.I. Pigment Green 7 and 36.

Particular preferred pigments are C.I. Pigment Brown 6 and 7.

Suitable pigments include mixed crystals of the above particular preferred pigments. Mixed crystals are also referred to as solid solutions. For example, under certain conditions different quinacridones mix with each other to form solid solutions, which are quite different from both physical mixtures of the compounds and from the compounds themselves. In a solid solution, the molecules of the components enter into the same crystal lattice, usually, but not always, that of one of the components. The x-ray diffraction pattern of the resulting crystalline solid is characteristic of that solid and can be clearly differentiated from the pattern of a physical mixture of the same components in the same proportion. In such physical mixtures, the x-ray pattern of each of the components can be distinguished, and the disappearance of many of these lines is one of the criteria of the formation of solid solutions. A commercially available example is Cinquasia Magenta RT-355-D from BASF AG.

Carbon black is preferred as a black pigment. Suitable black pigments include carbon blacks such as Pigment Black 7 (e.g. Carbon Black MA8® from MITSUBISHI CHEMICAL), Regal® 400R, Mogul® L, Elftex® 320 from CABOT Co., or Carbon Black FW18, Special Black 250, Special Black 350, Special Black 550, Printex® 25, Printex® 35, Printex® 55, Printex® 90, Printex® 150T from DEGUSSA. In a preferred embodiment, the carbon black pigment used is a pigment having less than 0.15% of toluene-extractable fraction using the method as described in section III, paragraph 5 of the Resolution AP(89) 1 dated 13 Sep. 1989 published by the Council of Europe.

It is also possible to make mixtures of pigments. For example, in some inkjet ink application a neutral black inkjet ink is preferred and can be obtained e.g. by mixing a black pigment and a cyan pigment into the ink. Also pigments may be combined to enlarge the colour gamut of an ink set. The inkjet application may also require one or more spot colours. Silver and gold are often desired colours for making a product more attractive by giving it an exclusive appearance.

Also non-organic pigments may be present in the inks. Suitable pigments are C.I. Pigment Metal 1, 2 and 3. Illustrative examples of the inorganic pigments include titanium oxide, barium sulfate, calcium carbonate, zinc oxide, lead sulfate, yellow lead, zinc yellow, red iron oxide (III), cadmium red, ultramarine blue, prussian blue, chromium oxide green, cobalt green, amber, titanium black and synthetic iron black. However, care should be taken to prevent migration and extraction of heavy metals in food application. In the preferred embodiment no pigments are used which contain a heavy metal selected from the group consisting of arsenic, lead, mercury and cadmium. In a more preferred embodiment, no inorganic pigments are used in the inkjet ink with the exception of titanium oxide, and calcium carbonate.

Pigment particles in inkjet ink should be sufficiently small to permit free flow of the ink through the inkjet-printing device, especially at the ejecting nozzles. It is also desirable to use small particles for maximum colour strength and to slow down sedimentation.

The numeric average pigment particle size is preferably between 0.050 and 1 µm, more preferably between 0.070 and 0.300 µm and particularly preferably between 0.080 and 0.200 µm. Most preferably, the numeric average pigment particle size is no larger than 0.150 µm. An average particle size smaller than 0.050 µm is less desirable for decreased light-fastness, but mainly also because very small pigment particles or individual pigment molecules thereof may still be extracted in food packaging applications.

The numeric average pigment particle size of pigment particles is best determined with a Brookhaven Instruments Particle Sizer BI90plus based upon the principle of dynamic light scattering. The ink is then diluted, for example, with ethyl acetate to a pigment concentration of 0.002 wt %. The measurement settings of the BI90plus are: 5 runs at 23° C., angle of 900, wavelength of 635 nm and graphics=correction function.

In the case of a white radiation curable ink, preferably a pigment with a refractive index greater than 1.60, preferably greater than 2.00, more preferably greater than 2.50 and most preferably greater than 2.60 is used. The white pigments may be employed singly or in combination.

Preferably titanium dioxide is used for the pigment with a refractive index greater than 1.60. Titanium oxide occurs in the crystalline forms of anatase type, rutile type and brookite type. The anatase type has a relatively low density and is easily ground into fine particles, while the rutile type has a relatively high refractive index, exhibiting a high covering power. Either one of these is usable in this invention. It is preferred to make the most possible use of characteristics and to make selections according to the use thereof. The use of the anatase type having a low density and a small particle size can achieve superior dispersion stability, ink storage stability and ejectability. At least two different crystalline forms may be used in combination. The combined use of the anatase type and the rutile type which exhibits a high colouring power can reduce the total amount of titanium oxide, leading to improved storage stability and ejection performance of ink.

For surface treatment of the titanium oxide, an aqueous treatment or a gas phase treatment is applied, and an alumina-silica treating agent is usually employed. Untreated-, alumina treated- or alumina-silica treated-titanium oxide are employable.

The numeric average particle diameter of the titanium oxide or other white pigments is preferably from 50 to 500 nm, more preferably from 150 to 400 nm, and most preferably from 200 to 350 nm. Sufficient hiding power cannot be obtained when the average diameter is less than 50 nm, and the storage ability and the jet-out suitability of the ink tend to be degraded when the average diameter exceeds 500 nm. The determination of the numeric average particle diameter is best performed by photon correlation spectroscopy at a wavelength of 633 nm with a 4 mW HeNe laser on a diluted sample of the pigmented inkjet ink. A suitable particle size analyzer used was a Malvern™ nano-S available from Goffin-Meyvis. A sample can, for example, be prepared by addition of one drop of ink to a cuvet containing 1.5 mL ethyl acetate and mixed until a homogenous sample was obtained. The measured particle size is the average value of 3 consecutive measurements consisting of 6 runs of 20 seconds.

Generally pigments are stabilized in the dispersion medium by dispersing agents, such as polymeric dispersants or surfactants. However, the surface of the pigments can be modified to obtain so-called "self-dispersible" or "self-dispersing" pigments, i.e. pigments that are dispersible in the dispersion medium without dispersants.

The pigment is preferably used in a pigment dispersion used for preparing inkjet inks in an amount of 10 to 40 wt %, more preferably of 15 to 30 wt % based on the total weight of the pigment dispersion. In a curable inkjet ink the pigment is preferably present in an amount of 0.1 to 20 wt %, preferably 1 to 10 wt % based on the total weight of the inkjet ink.

Polymeric Dispersants

Typical polymeric dispersants are copolymers of two monomers but may contain three, four, five or even more monomers. The properties of polymeric dispersants depend on both the nature of the monomers and their distribution in the polymer. Copolymeric dispersants preferably have the following polymer compositions:

statistically polymerized monomers (e.g. monomers A and B polymerized into ABBAABAB);

alternating polymerized monomers (e.g. monomers A and B polymerized into ABABABAB);

gradient (tapered) polymerized monomers (e.g. monomers A and B polymerized into AAABAABBABBB);

block copolymers (e.g. monomers A and B polymerized into AAAAABBBBBB) wherein the block length of each of the blocks (2, 3, 4, 5 or even more) is important for the dispersion capability of the polymeric dispersant;

graft copolymers (graft copolymers consist of a polymeric backbone with polymeric side chains attached to the backbone); and mixed forms of these polymers, e.g. blocky gradient copolymers.

Suitable polymeric dispersants are listed in the section on "Dispersants", more specifically [0064] to [0070] and [0074] to [0077], in EP 1911814 A (AGFA GRAPHICS) incorporated herein as a specific reference.

The polymeric dispersant has preferably a number average molecular weight Mn between 500 and 30000, more preferably between 1500 and 10000.

The polymeric dispersant has preferably a weight average molecular weight Mw smaller than 100,000, more preferably smaller than 50,000 and most preferably smaller than 30,000.

The polymeric dispersant has preferably a polydispersity PD smaller than 2, more preferably smaller than 1.75 and most preferably smaller than 1.5.

Commercial examples of polymeric dispersants are the following:
DISPERBYK™ dispersants available from BYK CHEMIE GMBH;
SOLSPERSE™ dispersants available from LUBRIZOL;
TEGO™ DISPERS™ dispersants from EVONIK;
EDAPLAN™ dispersants from MUNZING CHEMIE;
ETHACRYL™ dispersants from LYONDELL;
GANEX™ dispersants from ISP;
DISPEX™ and EFKA™ dispersants from BASF;
DISPONER™ dispersants from DEUCHEM.

Particularly preferred polymeric dispersants include Solsperse™ dispersants from LUBRIZOL, Efka™ dispersants from BASF and Disperbyk™ dispersants from BYK CHEMIE GMBH. Particularly preferred dispersants are Solsperse™ 32000, 35000 and 39000 dispersants from LUBRIZOL.

The polymeric dispersant is preferably used in an amount of 2 to 600 wt %, more preferably 5 to 200 wt %, most preferably 50 to 90 wt % based on the weight of the pigment.

Dispersion Synergists

A dispersion synergist usually consists of an anionic part and a cationic part. The anionic part of the dispersion synergist exhibiting a certain molecular similarity with the colour pigment and the cationic part of the dispersion synergist consists of one or more protons and/or cations to compensate the charge of the anionic part of the dispersion synergist.

The dispersion synergist is preferably added in a smaller amount than the polymeric dispersant(s). The ratio of polymeric dispersant/dispersion synergist depends upon the pigment and should be determined experimentally. Typically the ratio wt % polymeric dispersant/wt % dispersion synergist is selected between 2:1 to 100:1, preferably between 2:1 and 20:1.

Suitable dispersion synergists that are commercially available include Solsperse™ 5000 and Solsperse™ 22000 from LUBRIZOL.

Particular preferred pigments for the magenta ink used are a diketopyrrolo-pyrrole pigment or a quinacridone pigment. Suitable dispersion synergists include those disclosed in EP 1790698 A (AGFA GRAPHICS), EP 1790696 A (AGFA GRAPHICS), WO 2007/060255 (AGFA GRAPHICS) and EP 1790695 A (AGFA GRAPHICS).

In dispersing C.I. Pigment Blue 15:3, the use of a sulfonated Cu-phthalocyanine dispersion synergist, e.g. Solsperse™ 5000 from LUBRIZOL is preferred. Suitable dispersion synergists for yellow inkjet inks include those disclosed in EP 1790697 A (AGFA GRAPHICS).

Polymerization Inhibitors

The radiation curable composition or (inkjet) ink may contain a polymerization inhibitor. Suitable polymerization inhibitors include phenol type antioxidants, hindered amine light stabilizers, phosphor type antioxidants, hydroquinone monomethyl ether commonly used in (meth)acrylate monomers, and hydroquinone, t-butylcatechol, pyrogallol may also be used.

Suitable commercial inhibitors are, for example, Sumilizer™ GA-80, Sumilizer™ GM and Sumilizer™ GS produced by Sumitomo Chemical Co. Ltd.; Genorad™ 16, Genorad™ 18 and Genorad™ 20 from Rahn AG; Irgastab™ UV10 and Irgastab™ UV22, Tinuvin™ 460 and CGS20 from BASF; Floorstab™ UV range (UV-1, UV-2, UV-5 and UV-8) from Kromachem Ltd, Additol™ S range (S100, S110, S120 and S130) from Cytec Surface Specialties.

Since excessive addition of these polymerization inhibitors will lower the ink sensitivity to curing, it is preferred that the amount capable of preventing polymerization is determined prior to blending. The amount of a polymerization inhibitor is preferably lower than 2 wt % of the total radiation curable composition or (inkjet) ink.

In a preferred embodiment, the polymerization inhibitor is a polymerizable inhibitor, preferably containing one or more acrylate groups for achieving good reactivity.

Surfactants

The radiation curable composition or inkjet ink may contain at least one surfactant. The surfactant can be anionic, cationic, non-ionic, or zwitter-ionic and is preferably added in a total quantity less than 3 wt % based on the total weight of the ink and particularly in a total less than 1 wt % based on the total weight of the radiation curable composition or (inkjet) ink.

Preferred surfactants are selected from fluoro surfactants (such as fluorinated hydrocarbons) and silicone surfactants. The silicone surfactants are preferably siloxanes and can be alkoxylated, polyester modified, polyether modified, polyether modified hydroxy functional, amine modified, epoxy modified and other modifications or combinations thereof. Preferred siloxanes are polymeric, for example polydimethylsiloxanes.

Preferred commercial silicone surfactants include BYK™ 333 and BYK™ UV3510 from BYK Chemie.

In a preferred embodiment, the surfactant is a polymerizable compound.

Preferred polymerizable silicone surfactants include a (meth)acrylated silicone surfactant. Most preferably the (meth)acrylated silicone surfactant is an acrylated silicone surfactant, because acrylates are more reactive than methacrylates.

In a preferred embodiment, the (meth)acrylated silicone surfactant is a polyether modified (meth)acrylated polydimethylsiloxane or a polyester modified (meth)acrylated polydimethylsiloxane.

Preferred commercially available (meth)acrylated silicone surfactants include: Ebecryl™ 350, a silicone diacrylate from Cytec; the polyether modified acrylated polydimethylsiloxane BYK™ UV3500 and BYK™ UV3530, the polyester modified acrylated polydimethylsiloxane BYK™ UV3570, all manufactured by BYK Chemie; Tego™ Rad 2100, Tego™ Rad 2200N, Tego™ Rad 2250N, Tego™ Rad 2300, Tego™ Rad 2500, Tego™ Rad 2600, and Tego™ Rad 2700, Tego™ RC711 from EVONIK; Silaplane™ FM7711, Silaplane™ FM7721, Silaplane™ FM7731, Silaplane™ FM0711, Silaplane™ FM0721, Silaplane™ FM0725, Silaplane™ TM0701, Silaplane™ TM0701T all manufactured by Chisso Corporation; and DMS-R05, DMS-R11, DMS-R18, DMS-R22, DMS-R31, DMS-U21, DBE-U22, SIB1400, RMS-044, RMS-033, RMS-083, UMS-182, UMS-992, UCS-052, RTT-1011 and UTT-1012 all manufactured by Gelest, Inc.

Preparation of Radiation Curable Inkjet Inks

The preparation of pigmented radiation curable inkjet inks is well-known to the skilled person. Preferred methods of preparation are disclosed in paragraphs [0076] to [0085] of WO 2011/069943 (AGFA).

Inkjet Printing Methods

A radiation curable inkjet ink including a photoinitiator according to the invention is advantageously used for providing an inkjet printed packaging for food or pharma. However, the radiation curable inkjet ink is also suitable for other purposes such as printing on signs, displays and interior decoration.

A preferred inkjet printing method comprising the steps of: a) jetting a UV curable inkjet ink according to the invention on a substrate; and
b) at least partially UV curing the UV curable inkjet ink on the substrate with UV LEDs, preferably UV LEDS having an emission wavelength larger than 360 nm.

In a preferred embodiment, the UV curable inkjet ink is printed via a single pass printing operation.

In a preferred embodiment, the UV curable inkjet ink is cured by UV-LED radiation within 5 seconds of being printed.

In a preferred embodiment, the total UV-dose used to cure the UV curable inkjet inks is less than 300 $mJ/cm^2$.

The inkjet printing method results in a printed article. A preferred printed article includes a substrate and the UV curable inkjet ink as described above. The substrate is preferably selected from the group consisting of polyethylene terephthalate, aluminum, and glass.

Inkjet Printing Devices

The radiation curable inkjet ink may be jetted by one or more print heads ejecting small droplets in a controlled manner through nozzles onto a substrate, which is moving relative to the print head(s).

A preferred print head for the inkjet printing system is a piezoelectric head. Piezoelectric inkjet printing is based on the movement of a piezoelectric ceramic transducer when a voltage is applied thereto. The application of a voltage changes the shape of the piezoelectric ceramic transducer in the print head creating a void, which is then filled with ink. When the voltage is again removed, the ceramic expands to its original shape, ejecting a drop of ink from the print head. However the inkjet printing method according to the present invention is not restricted to piezoelectric inkjet printing. Other inkjet print heads can be used and include various types, such as a continuous type.

The inkjet print head normally scans back and forth in a transversal direction across the moving ink-receiver surface. Often the inkjet print head does not print on the way back. Bi-directional printing, also known as multi-pass printing, is preferred for obtaining a high areal throughput. Another preferred printing method is by a "single pass printing process", which can be performed by using page wide inkjet print heads or multiple staggered inkjet print heads which cover the entire width of the ink-receiver surface. In a single pass printing process the inkjet print heads usually remain stationary and the substrate surface is transported under the inkjet print heads.

Curing Devices

The radiation curable compositions, inks or inkjet inks according to the present invention can be cured by exposure to actinic radiation, preferably to ultraviolet radiation.

In inkjet printing, the curing means may be arranged in combination with the print head of the inkjet printer, travelling therewith so that the curing radiation is applied very shortly after jetting. Such rapid curing is sometimes referred to as "pin curing" and used for enhancing image quality by controlling the dot size. Preferably such curing means consists of one or more UV LEDs. In such an arrangement, it can be difficult to provide other types of curing means that are small enough to be connected to and travelling with the print head. Therefore, a static fixed radiation source may be employed, e.g. a source of curing UV-light, connected to the radiation source by means of flexible radiation conductive means such as a fibre optic bundle or an internally reflective flexible tube. Alternatively, the actinic radiation may be supplied from a fixed source to the radiation head by an arrangement of mirrors including a mirror upon the print head.

The source of radiation may also be an elongated radiation source extending transversely across the substrate to be cured. It may be adjacent the transverse path of the print head so that the subsequent rows of images formed by the print head are passed, stepwise or continually, beneath that radiation source.

Any ultraviolet light source, as long as part of the emitted light can be absorbed by the photo-initiator or photo-initiator system, may be employed as a radiation source, such as a high or low pressure mercury lamp, a cold cathode tube, a black light, an ultraviolet LED, an ultraviolet laser, and a flash light. Of these, the preferred source is one exhibiting a relatively long wavelength UV-contribution having a dominant wavelength of 300-400 nm. Specifically, a UV-A light source is preferred due to the reduced light scattering therewith resulting in more efficient interior curing.

UV radiation is generally classed as UV-A, UV-B, and UV-C as follows:
UV-A: 400 nm to 320 nm
UV-B: 320 nm to 290 nm
UV-C: 290 nm to 100 nm.

In a preferred embodiment, the inkjet printing device contains one or more UV LEDs with a wavelength larger than 360 nm, preferably one or more UV LEDs with a wavelength larger than 380 nm, and most preferably UV LEDs with a wavelength of about 395 nm.

Furthermore, it is possible to cure the image using, consecutively or simultaneously, two light sources of differing wavelength or illuminance. For example, the first UV-source can be selected to be rich in UV-C, in particular in the range of 260 nm-200 nm. The second UV-source can then be rich in UV-A, e.g. a gallium-doped lamp, or a different lamp high in both UV-A and UV-B. The use of two UV-sources has been found to have advantages e.g. a fast curing speed and a high curing degree.

For facilitating curing, the inkjet printing device often includes one or more oxygen depletion units. The oxygen depletion units place a blanket of nitrogen or other relatively inert gas (e.g. $CO_2$), with adjustable position and adjustable inert gas concentration, in order to reduce the oxygen concentration in the curing environment. Residual oxygen levels are usually maintained as low as 200 ppm, but are generally in the range of 200 ppm to 1200 ppm.

Substrates and Packaging

There is no real limitation on the type of substrate. The substrates may have ceramic, metallic, wood, paper or polymeric surfaces for printing. The substrate may also be primed, e.g. by a white primer or ink. However, the advantages of the radiation curable compositions and (inkjet) inks of the invention can be especially advantageously used on substrates for food packaging or pharmaceuticals. Food packaging is understood to include also packaging for liquids and drinks like milk, water, coke, beer, vegetable oil and the like.

The invention is advantageously used for providing food packaging, especially "primary" food packaging. Primary food packaging is the material that first envelops the product and holds it. This usually is the smallest unit of distribution or use and is the package which is in direct contact with the contents. Of course, for reasons of food safety, the radiation curable compositions and inkjet inks may also be used for secondary and tertiary packaging. Secondary packaging is outside the primary packaging, perhaps used to group primary packages together. Tertiary packaging is used for bulk handling, warehouse storage and transport shipping. The most common form of tertiary packaging is a palletized unit load that packs tightly into containers.

The substrate may be porous, as e.g. textile, paper and card board substrates, or substantially non-absorbing substrates such as e.g. a plastic substrate having a polyethylene terephthalate surface.

Preferred substrates including surfaces of polyethylene, polypropylene, polycarbonate, polyvinyl chloride, polyesters like polyethylene terephthalate (PET), polyethylene naphthalate (PEN) and polylactide (PLA) and polyimide.

The substrate may also be a paper substrate, such as plain paper or resin coated paper, e.g. polyethylene or polypropylene coated paper. There is no real limitation on the type of paper and it includes newsprint paper, magazine paper, office paper, wallpaper but also paper of higher grammage, usually referred to as boards, such as white lined chipboard, corrugated board and packaging board.

The substrates may be transparent, translucent or opaque. Preferred opaque substrates includes so-called synthetic paper, like the Synaps™ grades from Agfa-Gevaert which are an opaque polyethylene terephthalate sheet having a density of 1.10 g/cm$^3$ or more.

There is no restriction on the shape of the substrate. It can be a flat sheet, such a paper sheet or a polymeric film or it can be a three dimensional object like e.g. a plastic coffee cup. The three dimensional object can also be a container like a bottle or a jerry-can for including e.g. oil, shampoo, insecticides, pesticides, solvents, paint thinner or other type of liquids.

In a preferred embodiment, the substrate is a packaging, more preferably a food packaging, such as a wrapping for a chocolate bar.

EXAMPLES

Materials

All materials used in the following examples were readily available from standard sources such as Sigma-Aldrich (Belgium) and Acros (Belgium) unless otherwise specified. The water used is demineralized water.

Esacure™ KIP160 is a difunctional α-hydroxy-ketone photoinitiator supplied by Fratelli Lamberti SPA.

Irgacure™ 2959 is an α-hydroxy-ketone photoinitiator supplied by BASF.

TPO-L is ethyl phenyl(2,4,6-trimethylbenzoyl)phosphinate available as Omnirad™ TPO-L from IGM Resins BV.

THIOXANTHON-1 is a polymerisable thioxanthone, having the following structure and being a 50 wt % solution in VEEA. THIOXANTHON-1 was prepared according to example 1 of EP 2684876 A (AGFA):

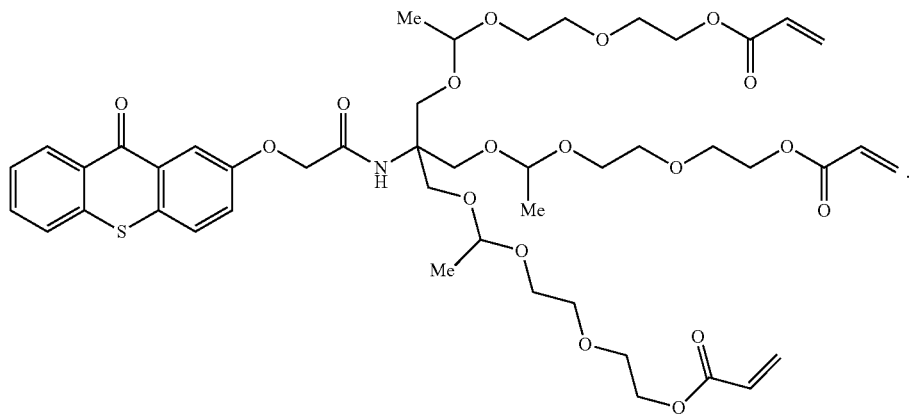 [SMILES: C=CC(=O)OCCOCCOC(C)OCC(COC(C)OCCOCCOC(=O)C=C)(COC(C)OCCOCCOC(=O)C=C)NC(=O)COc1ccc2sc3ccccc3c(=O)c2c1]

GENOPOL AB1 is a polymeric 4-dimethylaminobenzoic acid derivative supplied by Rahn.

VEEA is 2-(vinylethoxy)ethyl acrylate available from NIPPON SHOKUBAI, Japan.

INHIB is a mixture forming a polymerization inhibitor having a composition according to Table 2:

TABLE 2

| Component | wt % |
|---|---|
| VEEA | 82.4 |
| p-methoxyphenol | 4.0 |
| BHT | 10.0 |
| Cupferron™ AL | 3.6 |

Cupferron™ AL is aluminum N-nitrosophenylhydroxylamine from WAKO CHEMICALS LTD.

PET100 substrate is a 100 μm thick clear polyethylene terephthalate substrate available from AGFA-GEVAERT.

Measurement Methods

1. Molecular Mass

The molecular mass of a compound was determined using TLC-MS, according to the following procedure. A TLC was run under circumstances given in the synthetic examples. The TLC was analyzed using a CAMAG TLC-MS interface coupled to an AmaZon™ SL mass spectrometer (supplied by Bruker Daltonics) via an Agilent 1100 HPLC pump. First a blank spectrum was taken by eluting a spot on the TLC plate where no compounds are present with a 0.01 molar solution of ammonium acetate in methanol. A second spectrum of the compound to be analyzed was taken by eluting the spot of the compound under consideration with a 0.01 molar solution of ammonium acetate in methanol. The first spectrum was subtracted from the second spectrum, giving the spectrum of the compound to be analyzed.

Example 1

This example illustrates the synthesis of a photoinitiator according to the present invention.
Synthesis of INI-RAFT-1

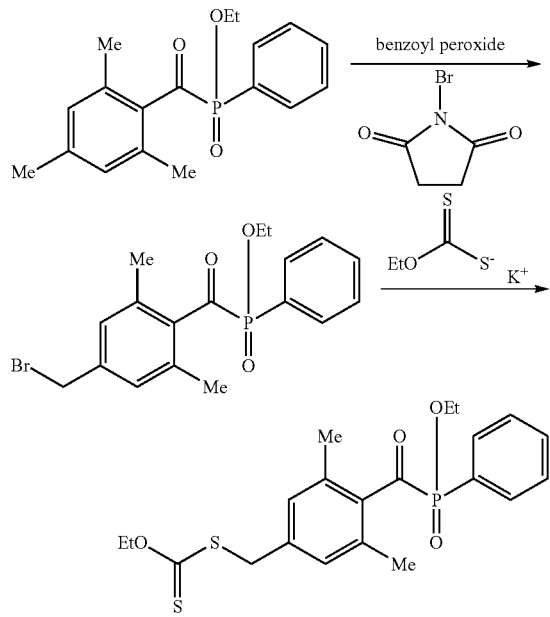

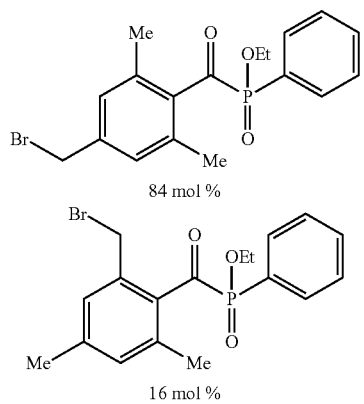

84 mol %

16 mol %

Step 1:
The bromination of 2,4,6-trimethylbenzoylethoxyphenylphosphine oxide to form (4-bromomethyl-2,6-dimethyl-benzoyl)-phenyl-phosphinic acid ethyl ester was conducted as follows:
119.57 g (0.378 mol) 2,4,6-trimethylbenzoylethoxyphenylphosphine oxide was dissolved in 500 ml acetonitrile. 67.28 g (0.378 mol) N-bromo-succinimid and 7.84 g (0.0324 mol) benzoyl peroxide were added and the mixture was heated to reflux. The mixture was refluxed for three hours. The mixture was allowed to cool down to room temperature and the solvent was removed under reduced pressure. The crude mixture was dissolved in 3600 ml methylene chloride and prepurified on a GraceResolve silica flash column using a gradient elution from methylene chloride to methylene chloride/ethyl acetate 93/7 to remove non eluting residues. 60 g of the crude 4-bromomethyl-2,6-dimethylbenzoylethoxyphenylphosphine oxide was isolated. 4-bromomethyl-2,6-dimethylbenzoylethoxyphenylphosphine oxide was purified by preparative chromatography on a Prochrom™ LC 80 column, using Kromasil™ 60 Å 10 μm as stationary phase and hexane-methyl tert. butyl ether (50/50) as eluent. 21.26 g 4-bromomethyl-2,6-dimethylbenzoylethoxyphenylphosphine oxide was isolated (TLC analysis TLC Silica gel 60F$_{254}$, supplied by MERCK, eluent hexane-methyl tert. butyl ether (50/50), R$_f$:0.17)).
$^1$H NMR analysis on a Varian 400 MHz Inova+spectrometer, using CDCl$_3$ as solvent and TMS as reference revealed that the isolated compound was an isomeric mixture of the following compounds Step 2:
6 g (15.2 mmol) (4-bromomethyl-2,6-dimethyl-benzoyl)-phenyl-phosphinic acid ethyl ester was dissolved in 45 ml ethanol and was added to a suspension of 3.8 g (24.2 mmol) ethyl xanthogenate potassium salt and 0.22 g (1.52 mmol) sodium iodide in 40 ml ethanol. The reaction mixture was heated to 78° C. for one hour. The mixture was allowed to cool down to room temperature. The precipitated salts were removed by filtration and the solvent was removed under reduced pressure. The crude RAFT-INI-1 was purified by preparative column chromatography on a Graceresolve column, using a gradient elution from methylene chloride to ethyl acetate. 1.2 g of RAFT-INI-1 was isolated (TLC analysis on Releveris™ RP C18-plates, supplied by GRACE, eluent methanol/1M NaCl 90/10, R$_f$:0.42). The molecular mass was confirmed using the TLC-MS methodology described above.

Example 2

This example illustrates the reduced extractability of RAFT functionalized acylphosphine oxides INI-RAFT-1. A comparison was made with the commercial photoinitiator TPO-L and a comparative RAFT functionalized photoinitiator COMP-RAFT-1.
Synthesis of COMP-RAFT-1 (Step 2)

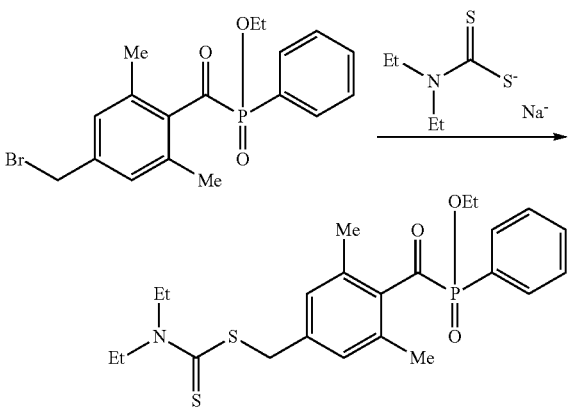

3 g (7.6 mmol) (4-bromomethyl-2,6-dimethyl-benzoyl)-phenyl-phosphinic acid ethyl ester was dissolved in 30 ml ethanol and was added to a solution of 2.74 g (12.2 mmol) diethyl dithiocarbamic acid sodium salt and 0.113 g (0.75 mmol) sodium iodide in 40 ml ethanol. The reaction mixture was heated to 78° C. for four hours. The mixture was allowed to cool down to room temperature. The solvent was removed under reduced pressure and the crude COMP-RAFT-1 was purified using preparative column chromatography on a Prochrom™ LC80 column, using Kromasil™ C18 100 Å 10 μm as silica and methanol/0.2 M ammonium acetate as eluent. 0.98 g of COMP-RAFT-1 was isolated (TLC analysis on Reveleris™ RP C18-plates, supplied by GRACE, eluent methanol/1M NaCl 80/20, $R_f$:0.32). The molecular mass was confirmed using the TLC-MS methodology described above.

Preparation of UV Curable inkjet Inks

The inventive UV curable inkjet ink INV-1 and comparative UV curable inkjet inks COMP-1 and COMP-2 were prepared according to Table 3. The weight percentages (wt %) were based on the total weight of the UV curable inkjet ink.

TABLE 3

| w % of component | COMP-1 | COMP-2 | INV-1 |
|---|---|---|---|
| TPO-L | 7 | — | — |
| COMP-RAFT-1 | — | 10 | — |
| INI-RAFT-1 | — | — | 9.5 |
| THIOXANTHON-1 | 20 | 20 | 20 |
| GENOPOL AB1 | 10 | 10 | 10 |
| VEEA | 62 | 59 | 59.5 |
| INHIB | 1 | 1 | 1 |

Evaluation and Results

For a quantitative extraction analysis of TPO-L, COMP-RAFT-1 and INI-RAFT-1 after UV curing, the UV curable inkjet inks INV-1, COMP-1 and COMP-2 were coated on a PET100 substrate using a bar coater and a 10 m wired bar. All coated samples were cured using a Fusion™ DRSE-120 conveyer, equipped with a Fusion™ VPS/1600 lamp (D-bulb). The samples were cured three times at a belt speed of 20 m/min at full power of the lamp. All samples were fully cured.

Two samples of 7.068 cm² of each sample were put into a 5 ml beaker and extracted twice with 2 ml acetonitrile, using ultrasound for 30 minutes. The extracts were transferred into a 5 ml volumetric flask. The samples were rinsed twice with a small amount of acetonitrile and the rinsing solvent was transferred into the 5 ml volumetric flask until the volume was adjusted to 5 ml. The solution was thoroughly mixed and filtered over a 0.25 m filter. 5 μl of each sample was injected on the HPLC.

An Alltima™ C18 column (150×3.2, 5 μm C18 silica), supplied by ALLTECH was used. The analysis was performed at 40° C. using water as Eluent A and acetonitrile as Eluent B using a gradient elution given by Table 4. A flow of 0.5 ml/min was used in combination with a UV-VIS detector at 204 nm.

TABLE 4

| Time (min) | % Eluent A | % Eluent B |
|---|---|---|
| 0 | 55 | 45 |
| 6 | 55 | 45 |
| 30 | 0 | 100 |
| 50 | 0 | 100 |
| 51 | 55 | 45 |
| 58 | 55 | 45 |

The results are summarized in Table 5.

TABLE 5

| Coated sample of | mg/m² |
|---|---|
| COMP-1 | 100 |
| COMP-2 | 127 |
| INV-1 | 25 |

From Table 5, it is clear that only a photoinitiator according to the present invention was capable of reducing the migration of the photoinitiator.

Example 3

This example illustrates the synthesis of photoinitiators according to the present invention.

Synthesis of INI-RAFT-2

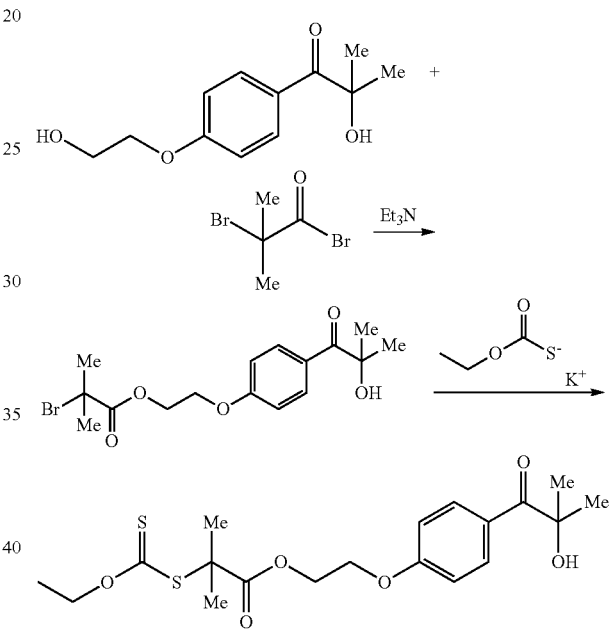

Step 1: Acylation of Irgacure™ 2959

9 g (40 mmol) Irgacure™ 2959 was dissolved in 150 ml ethyl acetate at 40° C. 4.45 g (44 mmol) triethyl amine was added. A solution of 9.20 g (40 mmol) 2-bromo-2-methyl-propionyl bromide in 25 ml ethyl acetate was added dropwise and the reaction was allowed to continue for 16 hours at room temperature. An additional 2.23 g (22 mmol) triethyl amine was added followed by the addition of 4.6 g (20 mmol) 2-bromo-2-methyl-propionyl bromide in 10 ml ethyl acetate. The reaction was allowed to continue for an additional hour at room temperature. The precipitated salts were removed by filtration. The ethyl acetate fraction was washed twice with a mixture of 50 ml water and 50 ml brine, dried over MgSO₄ and evaporated under reduced pressure. The acylation product was purified by preparative chromatography on a GraceResolve™ flash column, supplied by GRACE, using a gradient elution from hexane/methylene chloride 50/50 to methylene chloride/ethyl acetate 70/30. 8.8 g of acylated Irgacure™ 2959 was isolated (TLC analysis on TLC Silica gel 60F₂₅₄, supplied by MERCK, eluent hexane/ethyl acetate 70/30:$R_f$:0.23). The molecular mass was confirmed using the TLC-MS methodology described above.

Step 2: Substitution with Ethyl Xanthogenate Potassium Salt 3.37 g (10 mmol) 2-Bromo-2-methyl-propionic acid 2-[4-(2-hydroxy-2-methyl-propionyl)-phenoxy]-ethyl ester was dissolved in 16 ml dimethyl formamide. 2.56 g (16 mmol) ethyl xanthogenate potassium salt was added and the reaction was allowed to continue for 3 hours at 35° C. The reaction mixture was allowed to cool down to room temperature and 50 ml methyl t.butyl ether was added. The mixture was extracted three times with 50 ml water. The organic fraction was isolated and dried over $MgSO_4$. The solvent was evaporated under reduced pressure and INI-RAFT-2 was purified using preparative column chromatography on a Chromabond™ flash MN, supplied by MACHEREY-NAGEL GmbH, using hexane/ethyl acetate 70/30 as eluent. 1.1 g of INI-RAFT-2 was isolated (TLC analysis on Silica gel $60F_{254}$, supplied by MERCK, eluent hexane/ethyl acetate 70/30:$R_f$;0.25). The molecular mass was confirmed using the TLC-MS methodology described above.

Synthesis of INI-RAFT-9 allowed to continue for 16 hours at room temperature. The precipitated dicyclohexyl ureum was removed by filtration. The methylene chloride fraction was washed twice with 25 ml 1N hydrochloric acid and once with 25 ml water. The organic fraction was dried over $MgSO_4$ and the solvent was evaporated under reduced pressure. INI-RAFT-9 was purified with preparative column chromatography on a Chromabond™ flash MN column supplied by MACHEREY-NAGEL GmbH. 0.25 g of INI-RAFT-9 was isolated (TLC analysis on Silica gel $60F_{254}$, supplied by MERCK, eluent methylene chloride/ethyl acetate 90/10 $R_f$;0.44). The molecular mass was confirmed using the TLC-MS methodology described above.

Synthesis of INI-RAFT-4

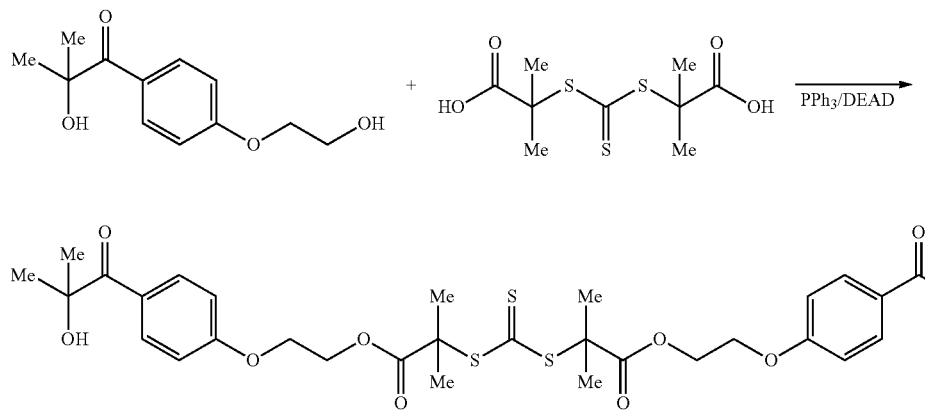

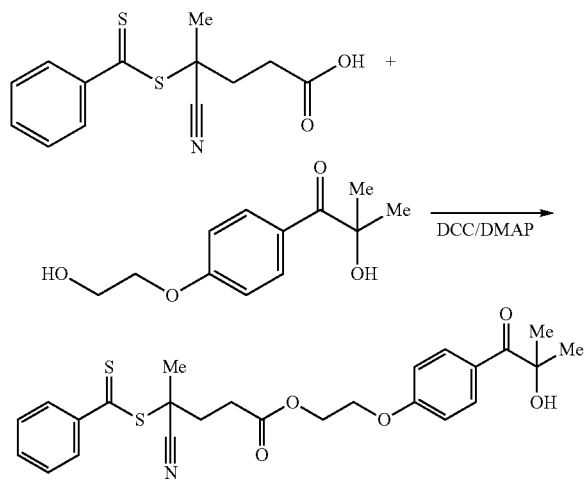

0.72 g (3.2 mmol) Irgacure™ 2959 and 0.89 g (3.2 mmol) 4-cyano-4-[(phenylthioxomethyl)thio]pentanoic acid were dissolved in 10 ml methylene chloride. The mixture was cooled to 0° C. and 1.32 g (6.4 mmol) dicyclohexyl carbodiimide and 0.08 g (0.64 mmol) 4-dimethylamino-pyridine in 5 ml methylene chloride were added. The reaction was The compound 2,2'-[carbonothioylbis(thio)]bis[2-methylpropanoic acid] was prepared according to Chakraborty et al., Macromolecules, 47(13), 4186-4198 (2014). 1.23 g (4.36 mmol) 2,2'-[carbonothioylbis(thio)]bis[2-methylpropanoic acid] and 3.93 g (15 mmol) triphenyl phosphine were dissolved in 25 ml THF. The mixture was stirred for 30 minutes at room temperature. 3.48 g (15.5 mmol) Irgacure™ 2959 in 25 ml THF was added and the mixture was cooled to 0° C. 6.53 g (15 mmol) of solution of 40 w % diethylazodicarboxylate in toluene was added while the temperature was kept below 10° C. The mixture was allowed to heat to room temperature and the reaction was allowed to continue for 16 hours at room temperature. The solvent was removed under reduced pressure and INI-RAFT-4 was purified by preparative column chromatography on a GraceResolve™ column, using a gradient elution from methylene chloride to methylene chloride/ethyl acetate 50/50. 0.65 g of INI-RAFT-4 was isolated (TLC analysis on LiChrospher™ RP-18W$F_{254s}$ supplied by MERCK, eluent methanol/1M NaCl:$R_f$;0.21). The molecular mass was confirmed using the TLC-MS methodology described above.

Example 4

This example illustrates the reduced extractability of RAFT functionalized α-hydroxy-ketones according to the present invention. The compounds COMP-RAFT-2, COMP-RAFT-3 and COMP-RAFT-4 were first prepared for allowing a fair comparison.

Synthesis of COMP-RAFT-2
Step 1: Tosylation of Irgacure™ 2959

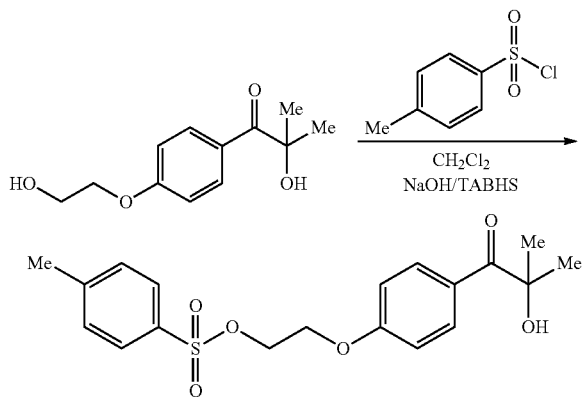

112.2 g (0.5 mol) Irgacure™ 2959 was suspended in 1 liter methylene chloride. 6.1 g (0.018 mol) tetrabutylammonium hydrogen sulfate was added and the mixture was stirred at room temperature. A solution of 62.4 g (1.56 mol) sodium hydroxide in 150 ml water was added while stirring. A solution of 103.9 g (0.545 mol) tosyl chloride in 300 ml methylene chloride and 5 ml dimethyl acetamide was added over 5 hours while keeping the temperature between 24 and 28° C. The reaction was allowed to continue for 2 hours at 20° C. The methylene chloride fraction was isolated and extracted twice with 500 ml water. The water fractions were extracted with 200 ml methylene chloride. The pooled methylene chloride fractions were dried over MgSO$_4$ and the solvent was removed under reduced pressure. The solid residue was treated with a mixture of 300 ml tert.butyl methyl ether and 200 ml hexane. The tosylate was isolated by filtration and treated for a second time with a mixture of 100 ml tert.butyl methyl ether and 200 ml hexane. The tosylate was isolated by filtration and dried. 173.8 g of the tosylate was isolated (yield: 92%, melting point 75° C.).

Step 2: Substitution of the Tosyl Group with Ethyl Xanthogenate Potassium Salt

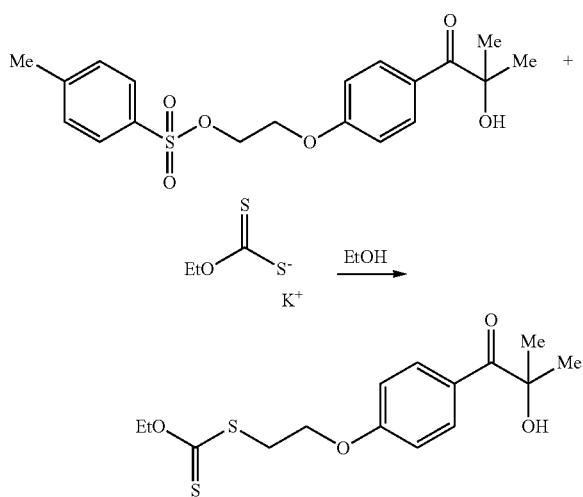

3.21 g (20 mmol) ethyl xanthogenate potassium salt was dissolved in 70 ml ethanol. A solution of 4.92 g (13 mmol) of tosylated Irgacure™ 2959 in 50 ml ethanol was added and the mixture was refluxed for two hours. The reaction mixture was allowed to cool down to room temperature. The formed salts were removed by filtration and the solvent was evaporated under reduced pressure. The residue was redissolved in 60 ml ethyl acetate. The ethyl acetate solution was extracted three times with a mixture of 30 ml water and 20 ml brine. The ethyl acetate fraction was isolated, dried over MgSO$_4$ and evaporated under reduced pressure. COMP-RAFT-2 was isolated using preparative column chromatography on a Prochrom™ LC80 column and Kromasil™ Si 60 µm 100 Å as silica, using a gradient elution from methylene chloride to methylene chloride/ethyl acetate 80/20. 1.5 g of COMP-RAFT-2 was isolated (TLC analysis on TLC Silica gel 60F$_{254}$, supplied by MERCK, eluent hexane/ethyl acetate 50/50:R$_f$:0.4) The molecular mass was confirmed using the TLC-MS methodology described above.

Synthesis of COMP-RAFT-3

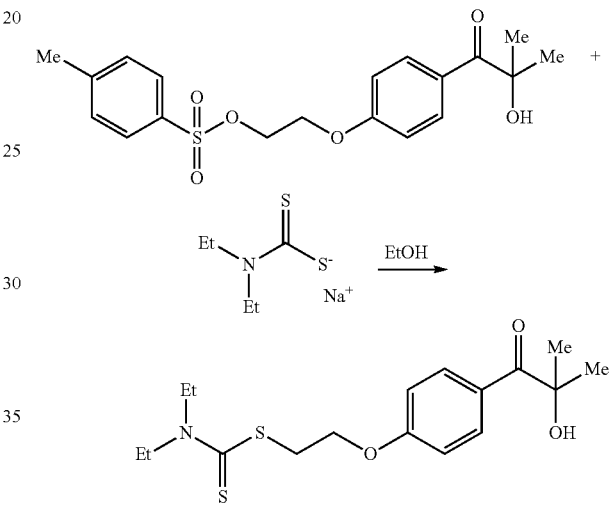

4.92 g (13 mmol) tosylated Irgacure™ 2959, 0.22 g (1.3 mmol) potassium iodide and 4.51 g (20 mmol) diethyldithio carbamic acid sodium salt were dissolved in 120 ml ethanol. The mixture was refluxed for two hours. The reaction mixture was allowed to cool down to room temperature and the solvent was removed under reduced pressure. The residue was redissolved in 60 ml ethyl acetate. The ethyl acetate fraction was extracted three times with a mixture of 30 ml water and 20 ml brine. The ethyl acetate fraction was dried over MgSO$_4$ and evaporated under reduced pressure. COMP-RAFT-3 was purified using preparative column chromatography on a Chromabond™ flash MN column, supplied by MACHEREY-NAGEL GmbH, and hexane/ethyl acetate 70/30 as eluent. 2.65 g of COMP-RAFT-3 was isolated (TLC analysis on TLC Silica gel 60F$_{254}$, supplied by MERCK, eluent hexane/ethyl acetate 70/30:R$_f$:0.37). The molecular mass was confirmed using the TLC-MS methodology described above.

Synthesis of COMP-RAFT-4

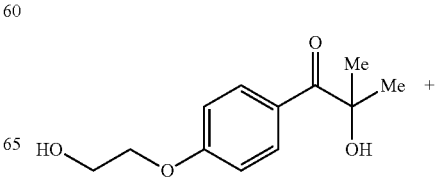

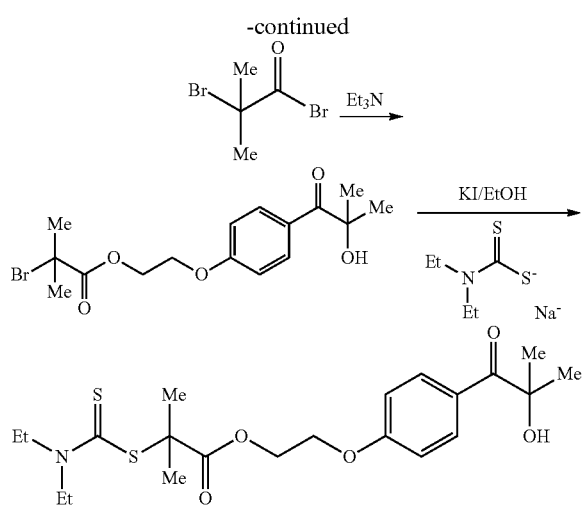

Step 1: acylation of Irgacure™ 2959

2-Bromo-2-methyl-propionic acid 2-[4-(2-hydroxy-2-methyl-propionyl)-phenoxy]-ethyl ester was prepared as described above for INI-RAFT-2.

Step 2: Substitution with Diethyldithio Carbamic Acid Sodium Salt 1.9 g (8.64 mmol) diethyldithio carbamic acid sodium salt and 90 mg (0.54 mmol) potassium iodide were dissolved in 30 ml ethanol. A solution of 2 g (5.4 mmol) acylated Irgacure™ 2959 in 20 ml ethanol was added and the mixture was refluxed for 9 hours. The reaction mixture was allowed to cool down to room temperature. The solvent was removed under reduced pressure and the residue was re-dissolved in 50 ml ethyl acetate. The precipitated salts were removed by filtration and the ethyl acetate fraction was extracted four times with a mixture of 30 ml water and 20 ml brine. The ethyl acetate fraction was dried over $MgSO_4$ and evaporated under reduced pressure. COMP-RAFT-4 was purified by preparative column chromatography on a GraceResolve™ flash column, supplied by GRACE, using a gradient elution from methylene chloride to methylene chloride/ethyl acetate 90/10. 1.1 g of COMP-RAFT-4 was isolated (TLC analysis on Silica gel $60F_{254}$, supplied by MERCK, eluent hexane/ethyl acetate 70/30 $R_f$:0.24). The molecular mass was confirmed using the TLC-MS methodology described above.

Preparation of UV Curable Inkjet Inks

The comparative UV curable inkjet inks COMP-3 to COMP-7 and the inventive UV curable inkjet inks INV-2 to INV-4 were prepared according to Table 6 respectively Table 7. The weight percentages (wt %) were based on the total weight of the UV curable inkjet ink.

TABLE 6

| wt % of | COMP-3 | COMP-4 | COMP-5 | COMP-6 | COMP-7 |
|---|---|---|---|---|---|
| Irgacure™ 2959 | 5 | — | — | — | — |
| Esacure™ KIP160 | — | 7.5 | — | — | — |
| COMP-RAFT-4 | — | — | 10 | — | — |
| COMP-RAFT-2 | — | — | — | 7.5 | — |
| COMP-RAFT-3 | — | — | — | — | 8 |
| TPO-L | 5 | 5 | 5 | 5 | 5 |
| THIOXANTHON-1 | 15 | 15 | 15 | 15 | 15 |
| Genopol™ AM | 10 | 10 | 10 | 10 | 10 |
| INHIB | 1 | 1 | 1 | 1 | 1 |
| VEEA | 64 | 61.5 | 59 | 61.5 | 61 |

TABLE 7

| wt % of | INV-2 | INV-3 | INV-4 |
|---|---|---|---|
| Irgacure™ 2959 | — | — | — |
| Esacure™ KIP160 | — | — | — |
| INI-RAFT-2 | 9 | — | — |
| INI-RAFT-9 | — | 11 | — |
| INI-RAFT-4 | — | — | 15 |
| TPO-L | 5 | 5 | 5 |
| THIOXANTHON-1 | 15 | 15 | 15 |
| Genopol™ AB1 | 10 | 10 | 10 |
| INHIB | 1 | 1 | 1 |
| VEEA | 60 | 58 | 54 |

Evaluation and Results

For a quantitative extraction analysis of COMP-RAFT-2 to COMP-RAFT-4 and INI-RAFT-2, INI-RAFT-4 and INI-RAFT-9 after UV curing, the UV curable inkjet inks INV-2 to INV-4 and COMP-3 and COMP-7 were coated on a PET100 substrate using a bar coater and a 10 μm wired bar. All coated samples were cured using a Fusion™ DRSE-120 conveyer, equipped with a Fusion™ VPS/1600 lamp (D-bulb). The samples were cured three times at a belt speed of 20 m/min at full power of the lamp. All samples were fully cured.

Two samples of 7.068 $cm^2$ of each sample were put into a 5 ml beaker and extracted twice with 2 ml acetonitrile, using ultrasound for 30 minutes. The extracts were transferred into a 5 ml volumetric flask. The samples were rinsed twice with a small amount of acetonitrile and the rinsing solvent was transferred into the 5 ml volumetric flask until the volume was adjusted to 5 ml. The solution was thoroughly mixed and filtered over a 0.25 m filter. 5 μl of each sample was injected on the HPLC.

An Alltima™ C18 column (150×3.2, 5 μm C18 silica), supplied by ALLTECH was used. The analysis was performed at 40° C. using water as Eluent A and acetonitrile as Eluent B using a gradient elution given by Table 8. A flow of 0.5 ml/min was used in combination with a UV-VIS detector at 204 nm.

TABLE 8

| Time (min) | % Eluent A | % Eluent B |
|---|---|---|
| 0 | 55 | 45 |
| 7 | 55 | 45 |
| 31 | 0 | 100 |
| 52 | 0 | 100 |
| 53 | 55 | 45 |
| 58 | 55 | 45 |

The results are summarized in Table 9.

TABLE 9

| Coated sample of | mg/$m^2$ |
|---|---|
| COMP-3 | 274 |
| COMP-4 | 384 |
| COMP-5 | 223 |
| COMP-6 | 323 |
| COMP-7 | 391 |
| INV-2 | 7.4 |
| INV-3 | 7.1 |
| INV-4 | 22.2 |

From Table 9, it becomes clear that only photoinitiators according to the present invention were capable of reducing the migration.

The invention claimed is:
1. A photoinitiator comprising:
a photoinitiator according to Formula (I):

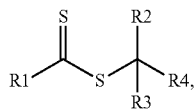

Formula (I)

wherein
R1 is selected from the group consisting of an alkyl group, an aryl group, a heteroaryl group, an alkenyl group, an alkynyl group, an alkaryl group, an aralkyl group, R5—O—, R6—S—, and a photoinitiating moiety selected from the group consisting of a thioxanthone group, a benzophenone group, an a-hydroxyketone group, an α-aminoketone group, an acylphosphine oxide group, and a phenyl glyoxalic acid ester group;
R2 is selected from the group consisting of hydrogen, an alkyl group, an aryl group, a heteroaryl group, an alkenyl group, an alkynyl group, an alkaryl group, and an aralkyl group;
R3 is selected from the group consisting of —C(=O)—O—R7, —C(=O)—NR8—R9, —C(=O)—R7, hydrogen, an alkyl group, an aryl group, a heteroaryl group, an alkenyl group, an alkynyl group, an alkaryl group, an aralkyl group, and a photoinitiating moiety selected from the group consisting of a thioxanthone group, a benzophenone group, an α-aminoketone group, an acylphosphine oxide group, and a phenyl glyoxalic acid ester group;
R4 is selected from the group consisting of —C(=O)—O—R10, —C(=O)—NR11—R12, —C(=O)—R10, a nitrile group, an aryl group, a heteroaryl group, and a photoinitiating moiety selected from the group consisting of a thioxanthone group, an α-aminoketone group, an acylphosphine oxide group, and a phenyl glyoxalic acid ester group;
R5 and R6 are independently selected from the group consisting of an alkyl group, an aryl or heteroaryl group, an alkenyl group, an alkynyl group, an alkaryl group, an aralkyl group, and a photoinitiating moiety selected from the group consisting of a thioxanthone group, a benzophenone group, an α-hydroxyketone group, an α-aminoketone group, an acylphosphine oxide group, and a phenyl glyoxalic acid ester group; and
R7, R8, R9, R11 and R12 are independently selected from the group consisting of hydrogen, an alkyl group, an aryl or heteroaryl group, an alkenyl group, an alkynyl group, an alkaryl group, an aralkyl group, and a photoinitiating moiety selected from the group consisting of a thioxanthone group, a benzophenone group, an α-hydroxyketone group, an α-aminoketone group, an acylphosphine oxide group, and a phenyl glyoxalic acid ester group, with the proviso that R8 and R9 and/or R11 and R12 may also represent atoms necessary to form a five or six membered ring;
R10 is selected from the group consisting of hydrogen, an alkyl group, an aryl or heteroaryl group, an alkenyl group, an alkynyl group, an alkaryl group, an aralkyl group, and a photoinitiating moiety selected from the group consisting of a thioxanthone group, an α-hy-droxyketone group, an α-aminoketone group, an acylphosphine oxide group, and a phenyl glyoxalic acid ester group;
and at least one of R1, R3, and R4 is functionalized with the photoinitiating moiety;
or
a photoinitiator selected from group consisting of:

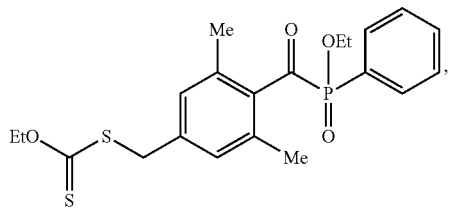

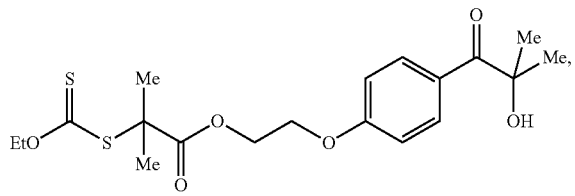

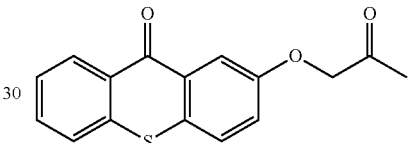

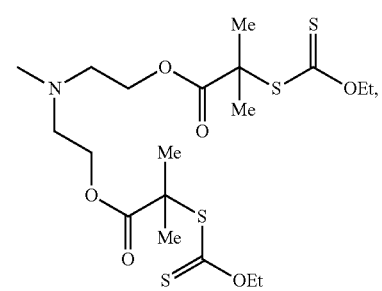

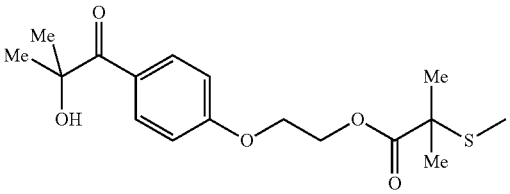

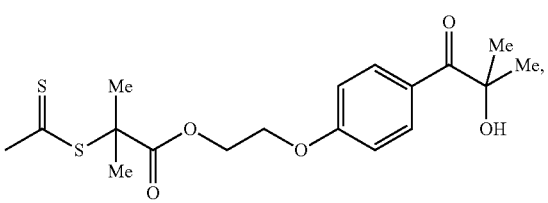

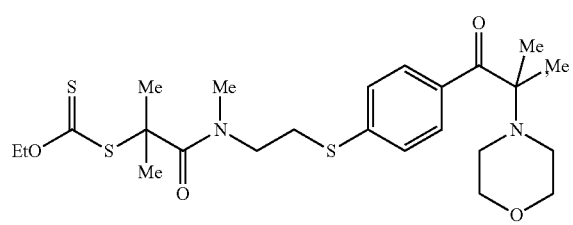

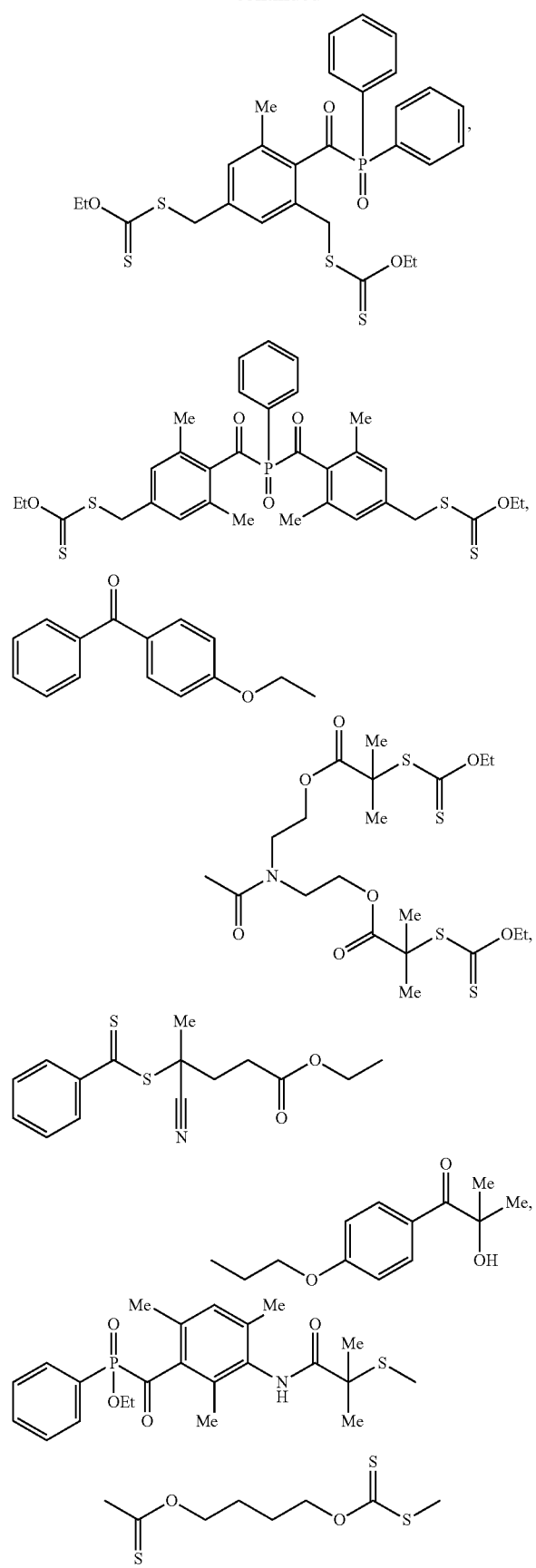
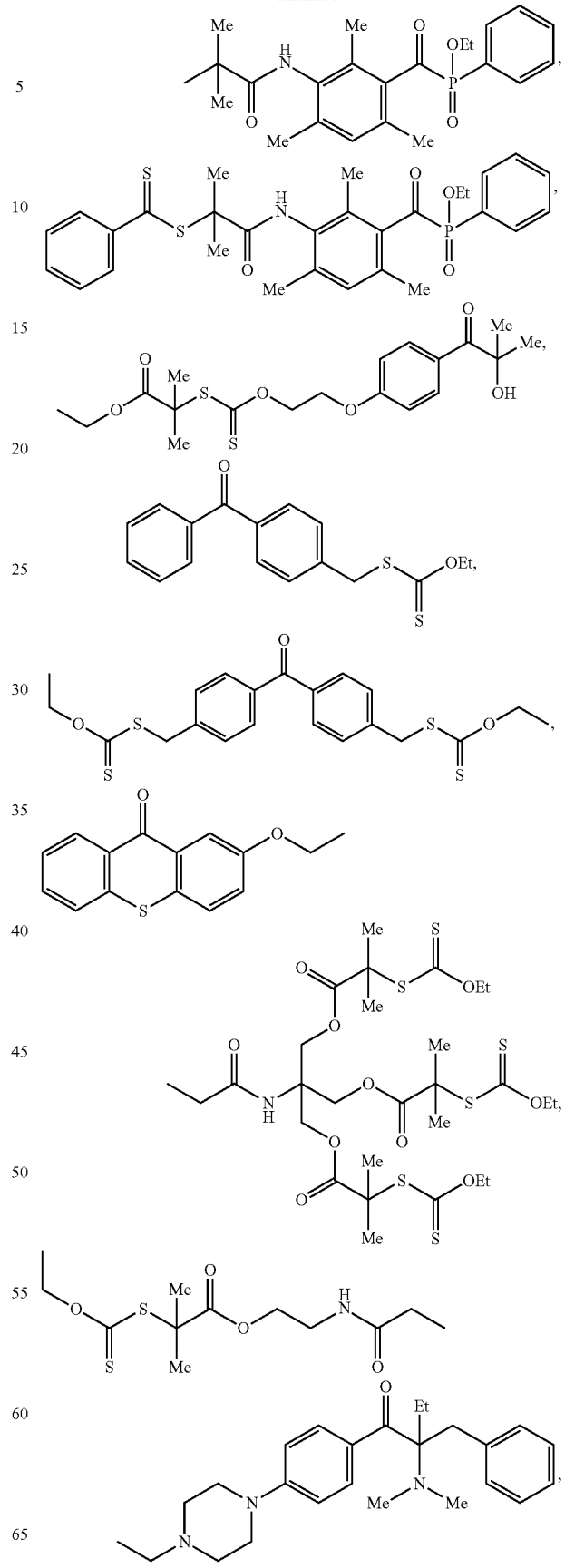

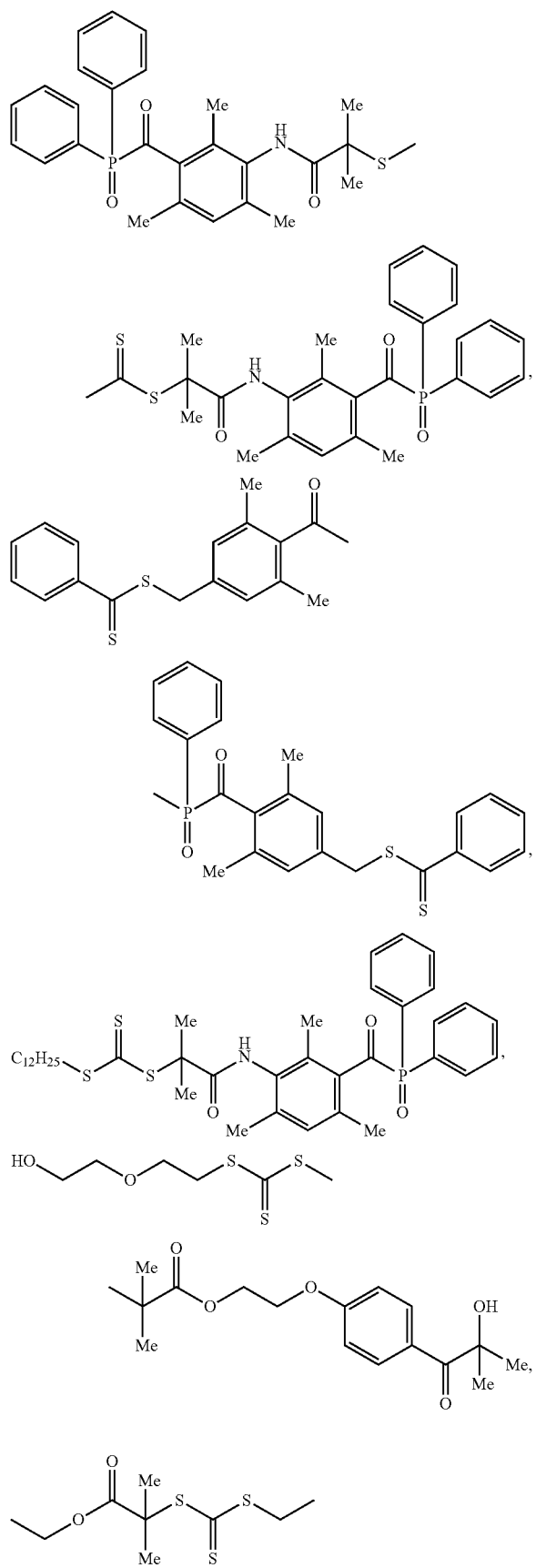

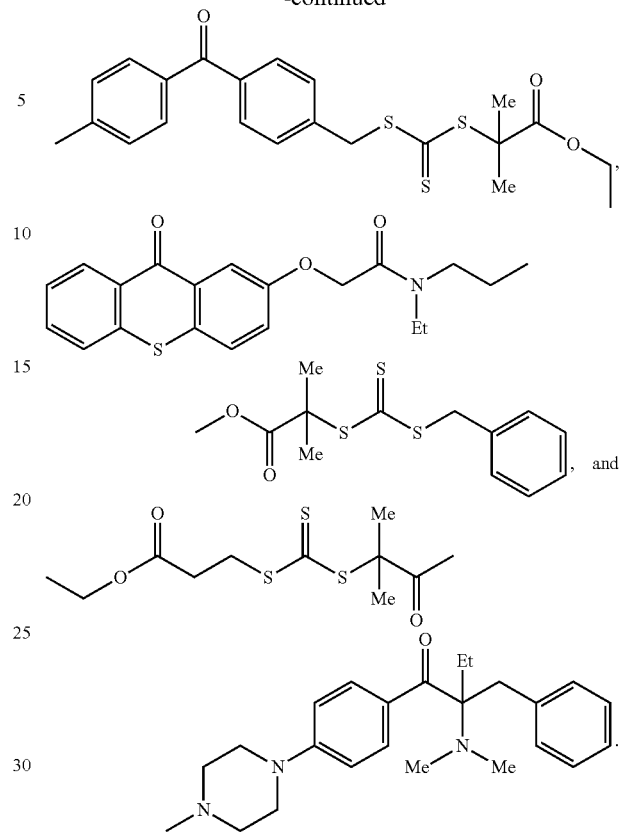

2. The photoinitiator according claim 1, wherein R1 is selected from the group consisting of an alkyl group, an aryl group, and a —O—R5 group.

3. The photoinitiator according to claim 2, wherein R1 is a —O—R5 group and R5 is selected from a C2 to C4 alkyl group.

4. The photoinitiator according to claim 1, wherein the photoinitiator according to Formula (I) includes a plurality of photoinitiating moieties.

5. The photoinitiator according to claim 4, wherein the plurality of photoinitiating moieties are independently selected from the group consisting of a thioxanthone group and an acylphosphine oxide group.

6. The photoinitiator according to claim 1, wherein the photoinitiator is a compound according to Formula (II):

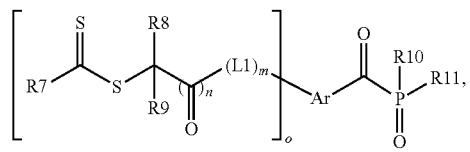

Formula (II)

wherein

R7 is selected from the group consisting of an alkyl group, an aryl, a heteroaryl group, an alkenyl group, an alkynyl group, an alkaryl group, an aralkyl group, O—R5, and —S—R6;

R5 and R6 are independently selected from the group consisting of an alkyl group, an aryl or heteroaryl group, an alkenyl group, an alkynyl group, an alkaryl group, an aralkyl group, and a photoinitiating moiety selected from the group consisting of a thioxanthone group, a benzophenone group, an α-hydroxyketone group, an α-aminoketone group, an acylphosphine oxide group, and a phenyl glyoxalic acid ester group;

Ar represents a carbocyclic arylene group;

L1 represents a divalent linking group including not more than 10 carbon atoms;

R8 and R9 are independently selected from the group consisting of hydrogen, an alkyl group, an aryl, a heteroaryl group, an alkenyl group, an alkynyl group, an alkaryl group, and an aralkyl group;

R10 is selected from the group consisting of an alkyl group, an aryl group, an alkoxy group, and an aryloxy group;

R11 is selected from the group consisting of an alkyl group, an aryl group, an alkoxy group, an aryloxy group, and an acyl group;

n and m represent 1 or 0;

o represents an integer from 1 to 5; and when n=0 and m=1, L1 is coupled to CR8R9 via a carbon atom of an aromatic or heteroaromatic ring.

7. The photoinitiator according to claim 1, wherein the photoinitiator is a compound according to Formula (III):

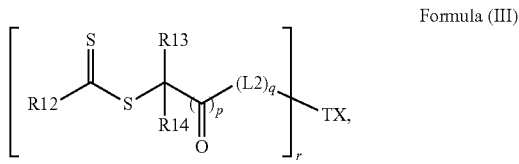

Formula (III)

wherein R12 is selected from the group consisting of an alkyl group, an aryl group, a heteroaryl group, an alkenyl group, an alkynyl group, an alkaryl group, an aralkyl group, —O—R5, and —S—R6;

R5 and R6 are independently selected from the group consisting of an alkyl group, an aryl group, a heteroaryl group, an alkenyl group, an alkynyl group, an alkaryl group, and an aralkyl group;

L2 represents a divalent linking group including not more than 20 carbon atoms;

TX represents a thioxanthone group;

p and q represent 1 or 0;

r represents an integer from 1 to 5;

R13 and R14 are independently selected from the group consisting of hydrogen, an alkyl group, an aryl or heteroaryl group, an alkenyl group, an alkynyl group, an alkaryl group, and an aralkyl group; and when p=0 and q=1, L2 is coupled to CR13R14 via a carbon atom of an aromatic or heteroaromatic ring.

8. The photoinitiator according to claim 1, wherein the photoinitiator is a compound according to Formula (IV):

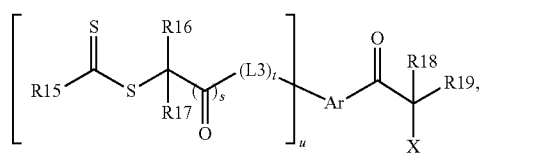

Formula (IV)

wherein

R15 is selected from the group consisting of an alkyl group, an aryl group, a heteroaryl group, an alkenyl group, an alkynyl group, an alkaryl group, an aralkyl group, —O—R5, and —S—R6;

R5 and R6 are independently selected from the group consisting of an alkyl group, an optionally substituted aryl or heteroaryl group, an alkenyl group, an alkynyl group, an alkaryl group, and an aralkyl group;

Ar represents an optionally substituted carbocyclic arylene group;

L3 represents a divalent linking group comprising not more than 20 carbon atoms;

R16 and R17 are independently selected from the group consisting of a hydrogen, an alkyl group, an aryl group, a heteroaryl group, an alkenyl group, an alkynyl group, an alkaryl group, and an aralkyl group;

R18 and R19 are independently selected from the group consisting of an alkyl group, an aryl group, an aralkyl group, and an alkaryl group, with the proviso that R18 and R19 may represent atoms necessary to form a five to eight membered ring;

X represents OH or NR2OR21;

R20 and R21 are independently selected from the group consisting of an alkyl group, an aryl group, an aralkyl group, and an alkaryl group, with the proviso that R20 and R21 may represent atoms necessary to form a five to eight membered ring;

s and t represent 1 or 0;

u represents an integer from 1 to 5; and when s=0 and t=1, L3 is coupled to CR16R17 via a carbon atom of an aromatic or heteroaromatic ring.

9. The photoinitiator according to claim 1, wherein the photoinitiator is a compound according to Formula (V):

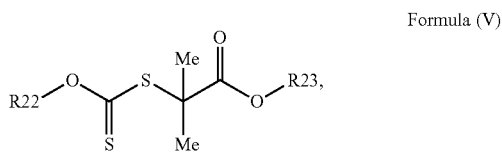

Formula (V)

wherein

R22 represents an alkyl group including no more than 6 carbon atoms; and

R23 represents a photoinitiating moiety selected from the group consisting of an acylphosphine oxide group, a thioxanthone group, a benzophenone group, an α-hydroxy ketone group, and an α-amino ketone group.

10. A radiation curable composition comprising:
the photoinitiator according to claim 1.

11. The radiation curable composition according to claim 10, wherein the radiation curable composition is a UV curable inkjet ink.

12. A method of manufacturing the photoinitiator according to claim 1 including a reversible addition-fragmentation chain transfer group, the method comprising:
reacting a compound comprising a photoinitiating moiety with an ethyl xanthogenate potassium salt, an ethyl xanthogenate sodium salt, an ethyl xanthogenate lithium salt, or an ethyl xanthogenate ammonium salt.

13. A method of inkjet printing comprising:
jetting one or more UV curable inkjet inks onto a substrate for packaging of food or pharma; wherein
each of the one or more UV curable inkjet inks includes the photoinitiator according to claim 1.

* * * * *